United States Patent [19]

Ueno

[11] Patent Number: 5,686,487
[45] Date of Patent: Nov. 11, 1997

[54] TREATMENT OF CATARACT WITH 15-KETO-PROSTAGLANDIN COMPOUNDS

[75] Inventor: Ryuji Ueno, Hyogo-ken, Japan

[73] Assignee: R-Tech Ueno Ltd., Osaka, Japan

[21] Appl. No.: 300,541

[22] Filed: Sep. 6, 1994

Related U.S. Application Data

[60] Continuation of Ser. No. 3,510, Jan. 12, 1993, abandoned, which is a division of Ser. No. 680,187, Apr. 3, 1991, Pat. No. 5,212,324.

[30] Foreign Application Priority Data

| Apr. 4, 1990 | [JP] | Japan | 2-90895 |
| Aug. 22, 1990 | [JP] | Japan | 2-221646 |
| Jan. 29, 1991 | [JP] | Japan | 3-29310 |

[51] Int. Cl.⁶ .................................................. A61K 31/557
[52] U.S. Cl. ............................................. 514/530; 514/573
[58] Field of Search ........................................ 514/530, 573

[56] References Cited

FOREIGN PATENT DOCUMENTS

| 330511 | 2/1988 | European Pat. Off. . |
| 343904 | 5/1988 | European Pat. Off. . |
| 308135 | 8/1988 | European Pat. Off. . |
| 281239 | 9/1988 | European Pat. Off. . |
| 284180 | 9/1988 | European Pat. Off. . |
| 310305 | 9/1988 | European Pat. Off. . |
| 289349 | 11/1988 | European Pat. Off. . |
| 292177 | 11/1988 | European Pat. Off. . |
| 310305 | 4/1989 | European Pat. Off. . |
| 342003 | 5/1989 | European Pat. Off. . |
| 345951 | 5/1989 | European Pat. Off. . |
| 330511 | 8/1989 | European Pat. Off. . |
| 342003 | 11/1989 | European Pat. Off. . |
| 343904 | 11/1989 | European Pat. Off. . |
| 345951 | 12/1989 | European Pat. Off. . |

OTHER PUBLICATIONS

Acta Physio. Scan, 66, 509–510–1966.

*Primary Examiner*—Robert Gerstl
*Attorney, Agent, or Firm*—Sughrue,Mion,Zinn,Macpeak & Seas

[57] ABSTRACT

A method for treatment of a cataract which comprises administering, to a subject in need of such treatment, a 15-ketoprostaglandin compound in an amount effective in treatment of cataract.

5 Claims, No Drawings

TREATMENT OF CATARACT WITH 15-KETO-PROSTAGLANDIN COMPOUNDS

The instant application is a Continuation of application Ser. No. 08/003,510 filed 12 Jan. 1993, now abandoned which is a divisional of application Ser. No. 07/680,187 filed 3 Apr. 1991 now U.S. Pat. No. 5,212,324.

BACKGROUND OF THE INVENTION

1. Field of the Invention

The present invention relates to a method for treatment of cataract which comprises administering a 15-ketoprostaglandin compound to a subject.

Prostaglandins (hereinafter, prostaglandins are referred to as PGs) are members of a class of organic carboxylic acid that are contained in human and most other mammalian tissues or organs and that exhibit a wide range of physiological activities. Naturally occurring PGs possess as a common structural feature the prostanoic acid skeleton:

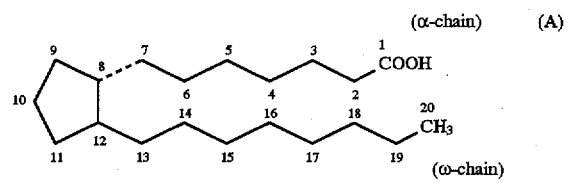

Some synthetic analogues have somewhat modified skeletons. The primary PGs are classified based on the structural feature of the five-membered cycle moiety into PGAs, PGBs, PGCs, PGDs, PGEs, PGFs, PGGs, PGHs and PGJs, and also on the presence or absence of unsaturation and oxidation in the chain moiety as:

| | |
|---|---|
| Subscript 1 | 13,14-unsaturated-15-OH |
| Subscript 2 | 5,6- and 13,14-diunsaturated-15-OH |
| Subscript 3 | 5,6- 13,14- and 17,18-triunsaturated-15-OH |

Further, PGFs are sub-classified according to the configuration of hydroxy group at position 9 into α(hydroxy group being in the alpha configuration) and β(hydroxy group being in the beta configuration).

2. Background Information

Naturally occurring $PGE_1$, $PGE_2$ and $PGE_3$ are known to have vasodilating, hypotensive, gastro-juice reducing, intestine-hyperkinetic, uterine contracting, diuretic, bronchodilating and anti-ulcer activities. Also, $PGF_{1\alpha}$, $PGF_{2\alpha}$ and $PGF_{3\alpha}$ are known to have hypertensive, vasocontracting, intestine-hyperkinetic, uterine contacting, luteo-regressive and bronchocontracting activities.

In addition, some 15-keto (i.e. having an oxo group at position 15 in place of the hydroxy group) prostaglandins and 13,14-dihydro-15-keto-prostaglandins are known as substances naturally produced by enzymatic actions during metabolism of primary PGs (Acta Physiologica Scandinavica, 66, 509, 1966). It has also been described that 15-keto-prostaglandin $F_{2\alpha}$ has an antipregnant activity.

European Patent Application No. 0,310,305 describes that 15-keto-PGs can be used as catharitics. However, it has not been reported that 15-keto-prostaglandin compounds have an activity useful in treatment of cataract.

As a result of extensive studies about the biological properties of 15-ketoprostaglandin compounds, the present inventor has discovered that these compounds are useful as an agent for treating cataract.

SUMMARY OF THE INVENTION

In a first aspect, the present invention provides a method for treatment of cataract which comprises administering, to a subject in need of such treatment, a 15-ketoprostaglandin compound in an amount effective in treatment of cataract.

In a second aspect, the present invention provides a use of a 15-ketoprostaglandin compound for the manufacture of a medicament for treatment of cataract.

In a third aspect, the present invention provides a pharmaceutical composition for treatment of cataract comprising a 15-ketoprostaglandin compound in association with a pharmaceutically acceptable carrier, diluent or excipient.

DETAILED DESCRIPTION OF THE INVENTION

Cataract is a disease characterized by an opacity of the crystalline lens of the eye. As used herein, the term "cataract" includes precataract which can be observed as an increase in intensity of scattered light in the crystalline lens, coloring of the crystalline lens, hardening of a nucleus of lens etc. According to the invention, 15-keto-PG compounds can be used in all the cataract, particularly in prophylaxis, i.e. prevention or inhibition of onset of cataract, regardless of its cause. Examples of cataract include senile cataract, traumatic cataract, nutritional cataract, diabetic cataract, toxic cataract, radiation cataract, etc.

As used herein, the term "treatment" or "treating" refers to any means of control of a disease in a mammal, including preventing the disease, curing the disease, relieving the disease and arresting or relieving the development of the disease.

The term "15-ketoprostaglandin compounds", referred to as 15-keto-PG compounds, include any prostaglandin derivatives which have an oxo group in place of the hydroxy group at position 15 of the prostanoic acid nucleus irrespective of the presence or absence of the double bond between positions 13 and 14.

NOMENCLATURE

Nomenclature of 15-keto-PG compounds herein uses the numbering system of prostanoic acid represented in formula (A) shown above.

While formula (A) shows a basic skeleton having twenty carbon atoms, the 15-keto-PG compounds used in the present invention are not limited to those having the same number of carbon atoms. The carbon atoms in Formula (A) are numbered 2 to 7 on the α-chain starting from the α-carbon atom adjacent to the carboxylic carbon atom which is numbered 1 and towards the five-membered ring, 8 to 12 on the said ring starting from the carbon atom on which the α-chain is attached, and 13 to 20 on the ω-chain starting from the carbon atom adjacent to the ring. When the number of carbon atoms is decreased in the α-chain, the number is deleted in order starting from position 2. and when the number of carbon atoms is increased in the α-chain, compounds are named as substituted derivatives having respective substituents at position 1 in place of carboxy group (C-1). Similarly, when the number of carbon atoms is decreased in the ω-chain, the number is deleted in order starting from position 20 and when the number of carbon atoms is increased in the ω-chain, compounds are named as substituted derivatives having respective substituents at position 20. Stereochemistry of the compounds is the same as that of above formula (A) unless otherwise specified. Thus, 15-keto-PG compounds having 10 carbon atoms in the ω-chain is nominated as 15-keto-20-ethyl-PGs.

The above formula expresses a specific configuration which is the most typical one, and in this specification compounds having such a configuration are expressed without any specific reference to it.

In general, PGDs, PGEs and PGFs have a hydroxy group on the carbon atom at position 9 and/or 11 but in the present specification the term "15-keto-PG compounds" includes PGs having a group other than a hydroxyl group at position 9 and/or 11. Such PGs are referred to as 9-dehydroxy-9-substituted-PG compounds or 11-dehydroxy-11-substituted-PG compounds.

As stated above, nomenclature of 15-keto-PG compounds is based upon the prostanoic acid. These compounds, however, can also be named according to the IUPAC naming system. For example, 13,14-dihydro-15-keto-16R,S-fluoro-PGE$_2$ is (Z)-7-{(1R,2R,3R)-3-hydroxy-2-[(4R,S)-fluoro-3-oxo-1-octyl]-5-oxocyclopentyl}-hept-5-enoic acid. 13,14-dihydro-15-keto-20-ethyl-11-dehydroxy-11R-methyl-PGE$_2$ methyl ester is methyl 7-{(1R,2S,3S)-3-methyl-2-[3-oxo-1-decyl]-5-oxocyclopentyl}-hept-5-enoate. 13,14-dihydro-6,15-diketo-19-methyl-PGE$_2$ ethyl ester is ethyl 7-{(1R,2S,3S)-3-hydroxy-2-(7-methyl-3-oxo-1-octyl)-5-oxocyclopentyl}-6-oxo-heptanoate. 13,14-dihydro-15-keto-20-ethyl-PGF$_{2\alpha}$ isopropyl ester is isopropyl (Z)-7-[(1R,2R,3R,5S)-3,5-dihydroxy-2-{3-oxo-1-decyl)-cyclopentyl]-hept-5-enoate. 13,14-dihydro-15-keto-20-methyl-PGF$_{2\alpha}$ methyl ester is methyl (Z)-7-[(1R,2R,3R,5S)-3,5-dihydroxy-2-{3-oxo-1-nonyl}-cyclopentyl]-hept-5-enonate.

PREFERRED COMPOUNDS

The 15-keto-PG compounds used in the present invention may be any derivatives of PG insofar as they have an oxo group at position 15 in place of the hydroxy group, and may have a double bond between positions 13 and 14 (15-keto-PG subscript 1 compounds), two double bonds between positions 13 and 14 as well as positions 5 and 6 (15-keto-PG subscript 2 compounds), or three double bonds between positions 13 and 14, positions 5 and 6 as well as positions 17 and 18 (15-keto-PG subscript 3 compounds), and may have a single bond between positions 13 and 14 (13,14-dihydro-15-keto-PG compounds).

Typical examples of the compounds used in the present invention are 15-keto-PGA, 15-keto-PGD, 15-keto-PGE, 15-keto-PGF, 13,14-dihydro-15-keto-PGA, 13,14-dihydro-15-keto-PGD, 13,14-dihydro-15-keto-PGE, and 13,14-dihydro-15-keto-PGF, wherein PG is as defined above as well as their substitution products or derivatives.

Examples of substitution products or derivatives include esters at the carboxy group at the alpha chain, pharmaceutically or physiologically acceptable salts, unsaturated derivatives having a double bond or a triple bond between positions 2 and 3 or positions 5 and 6, respectively, substituted derivatives having substituent(s) on carbon atom(s) at position 3, 5, 6, 16, 17, 19 and/or 20 and compounds having lower alkyl or a hydroxy (lower) alkyl group at position 9 and/or 11 in place of the hydroxy group, of the above PGs.

Examples of substituents present in preferred compounds are as follows: Substituents on the carbon atom at position 3, 17 and/or 19 include lower alkyl, for example, C$_{1-4}$ alkyl, especially methyl and ethyl. Substituents on the carbon atom at position 16 include lower alkyl e.g. methyl, ethyl etc., hydroxy and halogen atom e.g. chlorine, fluorine, aryloxy e.g. trifluoromethylphenoxy, etc. Substituents on the carbon atom at position 17 include halogen atom e.g. chlorine, fluorine etc. Substituents on the carbon atom at position 20 include saturated and unsaturated lower alkyl e.g. C$_{1-4}$ alkyl, lower alkoxy e.g. C$_{1-4}$ alkoxy and lower alkoxy (lower) alkyl e.g. C$_{1-4}$ alkoxy-C$_{1-4}$ alkyl. Substituents on the carbon atom at position 5 include halogen atom e.g. chlorine, fluorine etc. Substituents on the carbon atom at position 6 include oxo group forming carbonyl. Stereochemistry of PGs having hydroxy, lower alkyl or lower (hydroxy) alkyl substituent on the carbon atom at position 9 and/or 11 may be alpha, beta or mixtures thereof.

Said derivatives may have an alkoxy, phenoxy or phenyl group at the end of the omega chain where the chain is shorter than the primary PGs.

Especially preferred compounds are those having a lower alkyl e.g. methyl, ethyl etc., a halogen atom e.g. chloro, fluoro etc. at position 16, those having a halogen atom e.g. chloro, fluoro etc. at position 17, those having a lower alkyl e.g. methyl, ethyl etc. at position 19, those having a halogen atom e.g. chlorine, fluorine etc. at position 5, those having an oxo group at position 6, those having a lower alkyl, e.g. methyl, ethyl, etc. at position 20 and those having phenyl or phenoxy which are optionally substituted with halogen or haloalkyl at position 16 in place of the rest of the alkyl chain.

A group of preferred compounds used in the present invention has the formula

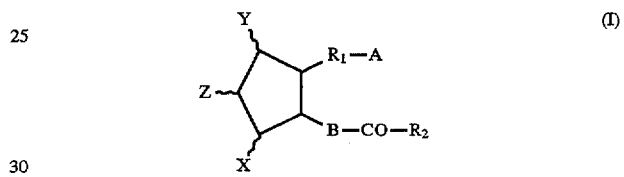

wherein X and Y are hydrogen, hydroxy, halo, lower alkyl, hydroxy(lower)alkyl, or oxo, with the proviso that at least one of X and Y is a group other than hydrogen, and 5-membered ring may have at least one double bond, Z is hydrogen or halo, A is —CH$_2$OH, —COCH$_2$OH, —COOH or its functional derivative, B is —CH$_2$—CH$_2$—, —CH═CH— or —C≡C—, R$_1$ is bivalent saturated or unsaturated, lower or medium aliphatic hydrocarbon residue which is unsubstituted or substituted with halo, oxo or aryl, R$_2$ is saturated or unsaturated, lower or medium aliphatic hydrocarbon residue which is unsubstituted or substituted with halo, hydroxy, oxo, lower alkoxy, lower alkanoyloxy, cyclo(lower)alkyl, aryl or aryloxy.

Among the compounds of the above formula, the compounds represented by the following formula are novel and form also part of the present invention.

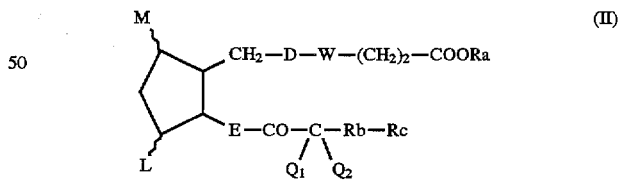

wherein

L and M are hydrogen atom, hydroxy, lower alkyl, hydroxy(lower)alkyl or oxo, provided that at least one of L and M is not hydrogen atom and that the five-membered ring may have one or two double bonds, Q$_1$ and Q$_2$ are hydrogen atom, halogen atom or lower alkyl, D is —CH$_2$—CH$_2$—, —CH═CH—, —C≡C— or —CO—CH$_2$—, E is —CH$_2$—CH$_2$— or —CH═CH—, W is —CH$_2$—CH$_2$—CH$_2$—, —CH═CH—CH$_2$ or —CH$_2$—CH═CH—, Ra is hydrogen atom, lower alkyl, cyclo(lower)alkyl, monocyclic aryl, monocyclic aryl(lower)alkyl or monocyclic aroyl(lower)alkyl, Rb is single bond or lower alkylene, Rc is lower alkyl which is unsubstituted or substituted with halogen, lower cycloalkyl which is unsubstituted or substituted with lower alkyl, monocyclic aryl which is unsubstituted or substituted with halogen or halo (lower)alkyl, or monocyclic aryloxy which is unsubstituted or substituted with halogen or halo(lower)alkyl, or a pharmaceutically acceptable salt when $R_1$ is hydrogen atom.

Since they have a specific profile that they have only part of action (e.g. an action treating cataract) of PGs while lacking the rest of action, they are useful as selective PGs-like agent.

In the above formula, the term "unsaturated" in the definitions for $R_1$ and $R_2$ is intended to include at least one and optionally more than one double bond and/or triple bond isolatedly, separately or serially present between carbon atoms of the main and/or side chains. According to usual nomenclature, an unsaturation between two serial positions is represented by denoting the lower number of said two positions, and an unsaturation between two distal positions is represented by denoting both of the positions. Preferred unsaturation is a double bond at position 2 and a double or triple bond at position 5.

It is preferred that the group —CH=CH— in D has cis configuration and the group —CH=CH— in E has trans configuration.

The term "lower or medium aliphatic hydrocarbon residue" refers to a straight or branched chain hydrocarbyl group having 1 to 14 carbon atoms (for a side chain, 1 to 3 carbon atoms being preferred) and preferably 2 to 8 carbon atoms for $R_1$ and 3 to 10 carbon atoms for $R_2$.

The term "halo" denotes fluoro, chloro, bromo and iodo.

The term "lower" throughout the specification is intended to include a group having 1 to 6 carbon atoms unless otherwise specified.

The term "lower alkyl" as a group or a moiety in hydroxy (lower)alkyl, monocyclic aryl(lower)alkyl, monocyclic aroyl(lower)alkyl or halo(lower)alkyl includes saturated and straight or branched chain hydrocarbon radicals containing 1 to 6, carbon atoms, e.g. methyl, ethyl, propyl, isopropyl, butyl, isobutyl, t-butyl, pentyl and hexyl.

The term "lower alkylene" refers to the group obtainable by removing a hydrogen atom from the lower alkyl group as defined above and includes e.g. methylene, ethylene, propylene (trimethylene), tetramethylene, 2-methyltetramethylene, pentamethylene, hexamethylene, etc.

The term "lower alkoxy" refers to the group lower-alkyl-O— wherein lower alkyl is as defined above.

The term "halo(lower)alkyl" refers to lower alkyl group as defined above which is substituted with at least one and preferably 1 to 3 halogen atoms as defined above and includes for example, chloromethyl, bromomethyl, fluoromethyl, trifluoromethyl, 1,2-dichloromethyl, 1,2,2-trichloroethyl, chloropropyl, chlorobutyl, chloropentyl, chlorohexyl etc.

The term "hydroxy(lower)alkyl" refers to lower alkyl as defined above which is substituted with at least one hydroxy group, e.g. hydroxymethyl, 1-hydroxyethyl, 2-hydroxyethyl and 1-methyl-1-hydroxyethyl.

The term "lower alkanoyloxy" refers to a group of the formula: RCO—O— wherein RCO—0 is an acyl group formed by oxidation of a lower alkyl group as defined above, e.g. acetyl.

The term "cyclo(lower)alkyl" refers to a cyclic group formed by cyclization of a lower alkyl group as defined above.

The term "aryl" includes unsubstituted or substituted aromatic carbocyclic or heterocyclic (preferably monocyclic) groups, e.g. phenyl, tolyl, xylyl and thienyl. Examples of substituents are halo and halo(lower)alkyl wherein halo and lower alkyl being as defined above.

The term "aryloxy" refers to a group of the formula: ArO— wherein Ar is aryl as defined above.

The term "monocyclic aryl" includes phenyl unsubstituted or substituted with lower alkyl substituent, for example phenyl, tolyl, xylyl, cumenyl etc.

The term "monocyclic aryloxy" refers to a group consisting of monocyclic aryl as defined above and bivalent oxygen —O— combined together, and includes, for example, phenoxy tolyloxy, xylyloxy, cumenyloxy etc.

The term "monocyclic aryl(lower)alkyl" refers to a group consisting of monocyclic aryl and lower alkyl, both as defined above, combined together, and includes, for example, benzyl, phenethyl, tolylmethyl etc.

The term "monocyclic aroyl(lower)alkyl" refers to a group consisting of monocyclic aroyl such as benzoyl unsubstituted or substituted with lower alkyl substituent and lower alkyl as defined above combined together, and includes phenacyl(benzoylmethyl), toluoylmethyl, xyloylmethyl, etc.

The term "functional derivative" of carboxy as A includes salts (preferably pharmaceutically acceptable salts), esters and amides.

Suitable "pharmaceutically acceptable salts" includes conventional non-toxic salts, and may be a salt with an inorganic base, for example an alkali metal salt (e.g. sodium salt, potassium salt, etc.) and an alkaline earth metal salt (e.g. calcium salt, magnesium salt, etc.), ammonium salt, a salt with an organic base, for example, an amine salt (e.g. methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, procaine salt, caffeine salt, etc.), a basic amino acid salt (e.g. arginine salt, lysine salt, etc.), tetraalkyl ammonium salt and the like. These salts can be prepared by the conventional process, for example from the corresponding acid and base or by salt interchange.

Examples of the esters are aliphatic esters, for example, lower alkyl ester e.g. methyl ester, ethyl ester, propyl ester, isopropyl ester, butyl ester, isobutyl ester, t-butyl ester, pentyl ester, 1-cyclopropylethyl ester, etc., lower alkenyl ester e.g. vinyl ester, allyl ester, etc., lower alkynyl ester e.g. ethynyl ester, propynyl ester, etc., hydroxy(lower)alkyl ester e.g. hydroxyethyl ester, lower alkoxy(lower)-alkyl ester e.g. methoxymethyl ester, 1-methoxyethyl ester, etc., and aromatic esters, for example, optionally substituted aryl ester e.g. phenyl ester, tosyl ester, t-butylphenyl ester, salicyl ester, 3,4-di-methoxyphenyl ester, benzamidophenyl ester etc., aryl(lower)alkyl ester e.g. benzyl ester, trityl ester, benzhydryl ester, etc. Examples of the amides are mono- or di-lower alkyl amides e.g. methylamide, ethylamide, dimethylamide, etc., arylamide e.g. anilide, toluidide, and lower alkyl- or aryl-sulfonylamide e.g. methylsulfonylamide, ethylsulfonyl-amide, tolylsulfonylamide etc.

Preferred examples of A include —COOH, —COOCH$_3$, —COOCH$_2$CH$_3$, —COOCH(CH$_3$)$_2$ and —CONHSO$_2$CH$_3$.

The configuration of the ring and the α- and/or omega chain in the above formula (I) may be the same as or different from that in the primary PGs. However, the present invention also includes a mixture of a compound having a primary configuration and that of an unprimary configuration.

Examples of the typical compounds of the present invention are 15-keto-PGs, 13,14-dihydro-15-keto-PGs and their e.g. 6-oxo-derivatives, $\Delta^2$-derivatives, 3R,S-methyl-derivatives, 5R,S-fluoro-derivatives, 5,5-difluoro-derivatives, 16R,S-methyl-derivatives, 16,16-dimethyl-derivatives, 16R,S-fluoro-derivatives, 16,16-difluoro-derivatives, 17S-methyl-derivatives, 17R,S-fluoro-derivatives, 17,17-difluoro-derivatives, 19-methyl-derivatives, 20-methyl-derivatives, 20-ethyl-derivatives, 19-desmethyl-derivatives, 2-decarboxy-2-carboxyalkyl derivatives and 16-desbutyl-16-phenoxy derivatives.

When 15-keto-PG compounds of the present invention have a saturated bond between positions 13 and 14, these compounds may be in the keto-hemiacetal equilibrium by forming a hemiacetal between hydroxy group at position 11 and ketone at position 15.

The proportion of both tautomeric isomers, when present, varies depending on the structure of the rest of the molecule or kind of any substituent present and, sometimes, one isomer may predominantly be present in comparison with the other. However, in this invention, it is to be appreciated that the compounds used in the invention include both isomers. Further, while the compounds used in the invention may be represented by a structure or name based on keto-form regardless of the presence or absence of the isomers, it is to be noted that such structure or name does not intend elimination of the hemiacetal type of compounds.

In the present invention, any of the individual tautomeric isomers, a mixture thereof, or optical isomers, a mixture thereof, a racemic mixture, and other isomers such as steric isomers can be used in the same purpose.

Some of the compounds used in the present invention may be prepared by the method disclosed in Japanese Patent Publications (unexamined) No. A-52753/1989, A-104040/1989, A-151519/1989.

Alternatively, these compounds may be prepared by a process analogous to that described herein or to known processes.

A practical preparation of the 15-keto compounds involves the following steps; referring to the Synthetic Charts I to III, reaction of the aldehyde (2) prepared by the Collins oxidation of commercially available (−)-Corey lactone (1) with dimethyl (2-oxoheptyl)phosphate anion to give α,β-unsaturated ketone (3), reduction of the α,β-unsaturated ketone (3) to the corresponding saturated ketone (4), protection of the carbonyl group of the ketone (4) with a diol to the corresponding ketal (5), and deprotection of the p-phenylbenzoyl group to give the corresponding alcohol (6) followed by protection of the newly derived hydroxy group with dihydropyrane to give the corresponding tetrahydropyranyl ether (7). According to the above process, a precursor of PGEs wherein the ω-chain is a 13,14-dihydro-15-keto-alkyl group is prepared.

Using the above tetrahydropyranyl ether (7), 6-keto-PGE₁s (15) of which a group constituted with carbon atoms at positions 5, 6 and 7 is —₅CH₂—₆C(O)₇—CH₂—, may be prepared in the following steps; reduction of the tetrahydropyranyl ether (7) with, for example, diisobutyl aluminum hydride to give the corresponding lactol (8), reaction of the lactol (8), with the ylide generated from (4-carboxybutyl) triphenyl phosphonium bromide followed by esterification (10), cyclization between the 5,6-double bond and the hydroxyl group at position 9 with NBS or iodine to give the halogenated compound (11), dehydrohalogenation of the compound (11) with, for example, DBU to give the 6-keto compound (13) followed by Jones oxidation and removal of the protecting groups.

Furthermore, PGE₂s (19) of which a group constituted with carbon atoms at positions 5, 6 and q 7 is —₇CH₂—₆CH=₅CH— may be prepared in the following steps; as shown in the Synthetic Chart II, reduction of the above tetrahydropyranyl ether (7) to give the lactol (8), reaction of the resultant lactol (8) with the ylide derived from (4-carboxybutyl-)triphenyl phosphonium bromide to give the carboxylic acid (16) followed by esterification to give ester (17), Jones oxidation of the esters (17) to give the compound (18), and removal of the protecting groups.

Using the above tetrahydropyranyl ether (7) as the starting material, the compound having —₇CH₂—₆CH₂—₅CH₂— may be prepared by using the same process as that for preparing PGE₂ having —CH₂CH=CH— and subjecting the resultant compound (18) to catalytic reduction to reduce the double bond between the positions 5 and 6 followed by removal of the protective groups.

Synthesis of 5,6-dehydro-PGE₂s having —₇CH₂—₆C≡₅C— may be carried out by capturing a copper enolate formed by 1,4-addition of a monoalkylcopper complex or a dialkylcopper complex of the following formulae:

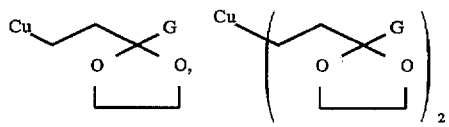

wherein G is alkyl, to 4R-t-butyldimethylsilyloxy-2-cyclopenten-1-one with 6-alkoxycarbonyl-1-iodo-2-hexyne or the derivatives.

The 11-β type PGEs can be prepared according to the Synthetic Chart III.

PGE derivatives having a methyl group at position 11 in place of hydroxy can be prepared by reacting a dimethylo copper complex with PGA-type compound obtained by subjecting 9-hydroxy-11-tosylate to the Jones oxidation. Alternatively, they can be prepared by protecting the carbonyl of saturated ketone (4) produced by reducing unsaturated ketone (3), eliminating p-phenylbenzoyl and tosylating the produced alcohol, treating with DBU to form a lactol, introducing the alpha-chain by Wittig reaction, oxidizing the alcohol at position 9 to give PGA-type compound, and reacting the product with dimethyl copper complex in order to introduce a methyl group into position 11 to give an 11-methyl-PGE-type compound, which on reduction with e.g. sodium borohydride gives an 11-methyl-PGF-type compound. An 11-hydroxymethyl-PGE-type compound, is obtained by a benzophenone-sensitized photoaddition of methanol of PGA-type compound, which is reduced with, e.g. sodium borohydride, to give an 11-hydroxymethyl-PGF-type compound. The 16-mono- or 16,16-di-halo type PGEs can be prepared according to the synthetic chart IV. The synthetic route for the compounds used in the present invention is not limited to the that described above one and may vary using different protecting, reducing and/or oxidizating methods.

Furthermore, the novel compounds of the formula II may be prepared by processes shown in the following Synthetic Charts V to XIII, wherein P₁, P₂, P₃, P₄, P₅, P₆ and P₇ are each protective groups and Q₁, Q₂, Rb and Rc are the same as defined above.

Referring to Synthetic Chart V, the compound (41) (for example, a compound wherein Q₁ and Q₂ are hydrogen is the compound 8 described in Synthetic Chart I on page 37 of JP-A-52753/1989) is reacted with a ylid produced from (6-carboxyhexyl)triphenylphosphonium bromide to form the compound (42), which is esterified to give the compound (43), which, on removal of the protective groups, can give the compound (44). Also, referring to Synthetic Chart VI, the above compound (43) is oxidized by Jones oxidation to form the compound (45), which can be given the compound (46) by removing the protective groups. The compounds wherein W is —CH=CH—CH$_2$— or —CH$_2$—CH=CH— can be prepared by reacting the compound (41) with a ylid produced from (6-carboxy-2-hexenyl) triphenylphosphonium bromide or (6-carboxy-3-hexenyl) triphenylphosphonium bromide, respectively, and the treating the formed compound in a manner similar to that above.

In another example, referring to Synthetic Chart VII, the compound (48), obtained by deprotecting the compound (47) which is commercially available, is oxidized by Swern oxidation to give the aldehyde (49), which is reacted with 2-oxoheptyl phosphonate (for example, 3,3-dihalogenated derivative) to give the compound (50). Catalytic reduction of it gives the compound (51), the ketone moiety of which is reduced by sodium borohydride to form the compound (52). This is further reduced by diisobutylaluminum hydride to give the lactol (53). On reaction with carboxyhexylphosphonium bromide, it gives the compound (54), which is esterified to the compound (55), oxidized to the compound (56) and deprotected to the compound (46). If desired, this can be hydrolyzed to the free acid (57). Also, in the Synthetic Chart VIII, the above compound (55) can be catalytically hydrogenated to form the compound (58), which is oxidized by Swern oxidation to give the compound (59) and then deprotected to form the desired compound (60).

In the above process, when the reduction in the step from the compound (50) to the compound (41) is omitted, a compound wherein Z is —CH=CH— is obtained.

Further, when the compounds of the formula (I) wherein L is other than OH (for example, lower alkyl) are desired, the lactone moiety in the compound obtained by removing the protective group at position 11 and introducing a protective group in position 15 of the compound (52) is reduced to lactol and then an α-chain is introduced to the product by Wittig reaction. Then the hydroxy group at position 11 is protected by a lower alkane- or monocyclic aryl-sulfonate group and the product is subjected to oxidation (for example, Jones) to give 10-en-9-one compound, which is reacted with lower alkyl lithium to form a 11-lower alkyl compound. Compounds of PGD-type can be obtained by oxidizing the 11-deprotected compounds. Compounds of PGA-type can be obtained from the 10-en-9-one compounds. In addition, as shown in Synthetic Chart IX, 6-keto compounds can be obtained by reacting the compound (43) with N-bromosuccinimide or iodine to from the compound (61), followed by treatment with DBU. The 5,6-dehydro (i.e. acetylenic) compounds can be prepared, according to Synthetic Chart X, by reacting the copper enolate, formed by reacting the compound (63) with a copper complex, with 8-alkoxycarbonyl-1-iodo-2-octyne. Saturated α-chain introducing agent are prepared as shown in Synthetic Chart XI.

In a further example, according to Synthetic Chart XII, the hydroxy group at position 15 of the compound (52) is protected (for example, by silyl protective group) to form the compound (65) and lactone moiety of which is reduced to lactol giving the compound (66), which is then reacted with an α-chain introducing agent (for example, a ylid produced from (6-carboxyhexyl)triphenyl phosphonium bromide) to give the compound (67). Then the carboxy group is protected to form the compound (68) and the hydroxy group at position 9 is protected to form the compound (69). The protective group at position 15 is removed to give the compound (70), which is oxidized to the compound (71). Deprotection at positions 9 and 11 gives the desired compound (72).

Further, as shown in Synthetic Chart XIII, the compound (54) obtained as in Synthetic Chart VII is protected with a protective group removable by catalytic hydrogenation (for example, benzyl) to form the compound (55), which is oxidized at position 9 and deprotected at position 11 to give the compound (46). Catalytic hydrogenation of this compound gives the desired compound (73).

Corresponding other PG compounds can be produced analogously.

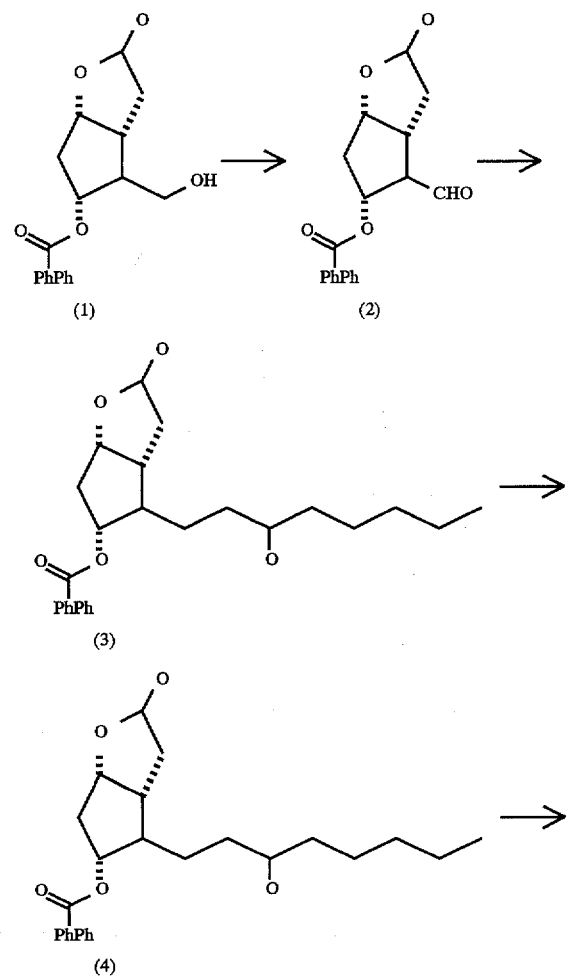

Synthetic Chart I (1)

(2)

(3)

(4)

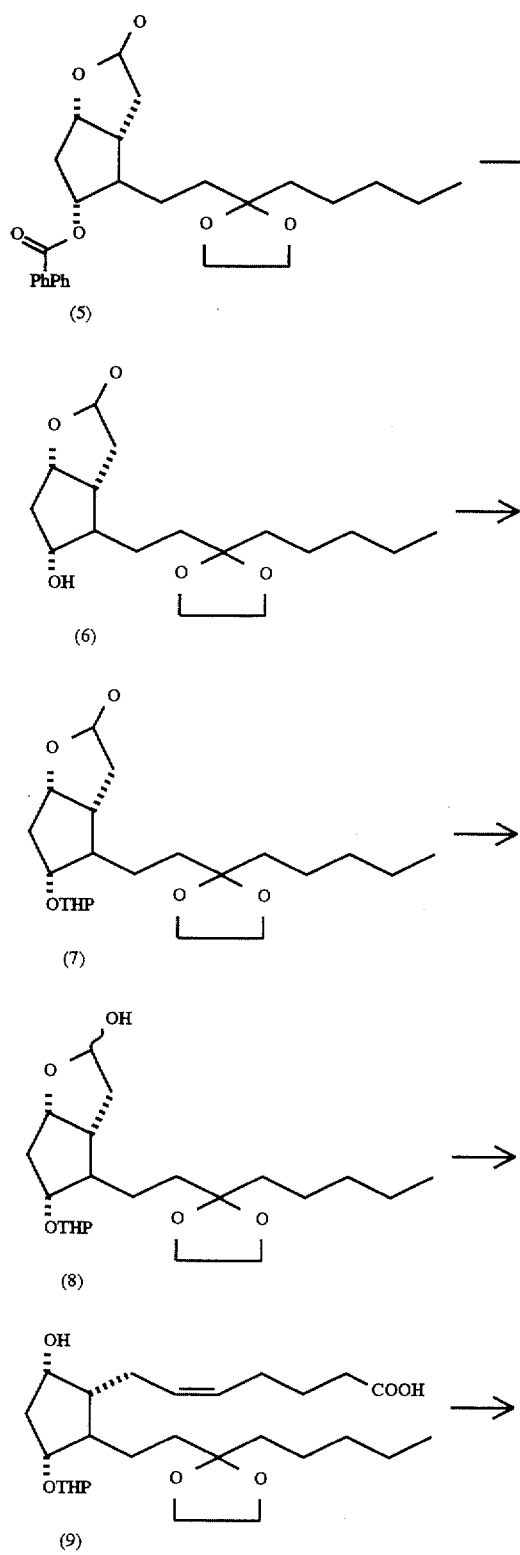
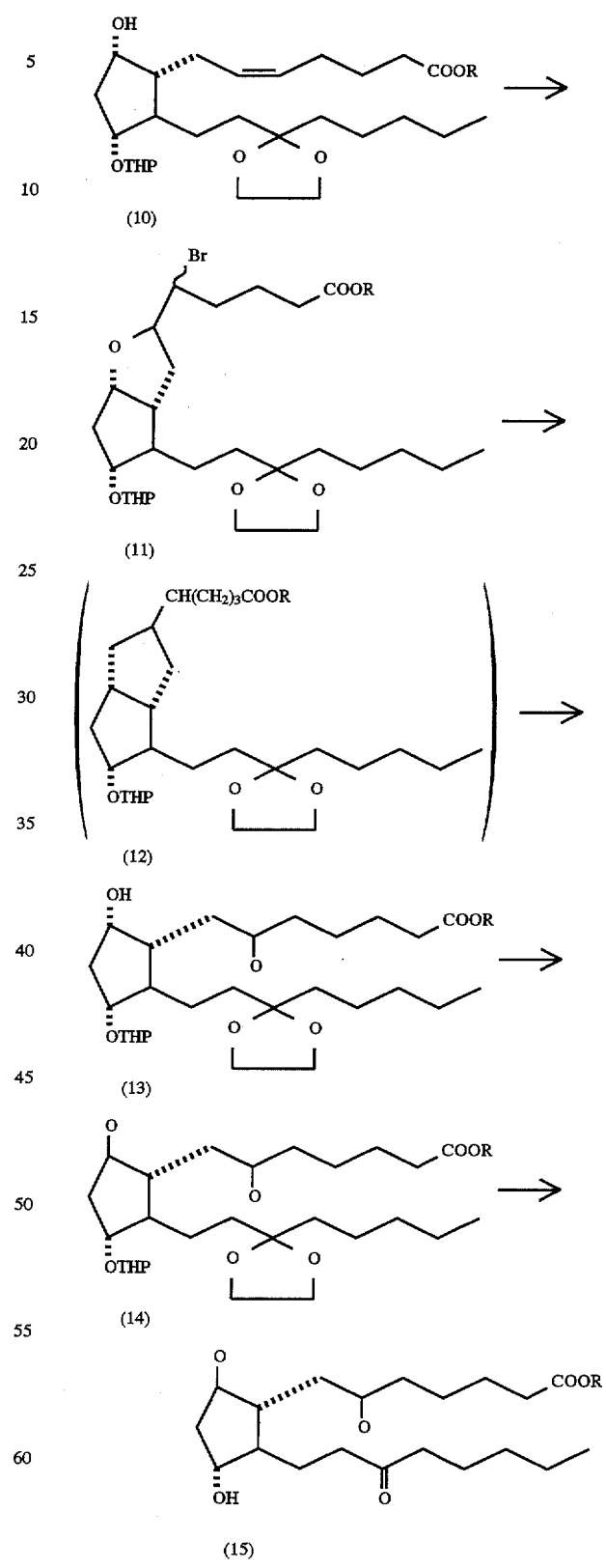

Synthetic Chart I
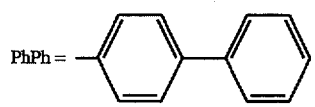
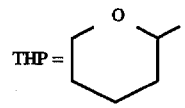
R = lower alkyl
Synthetic Chart II
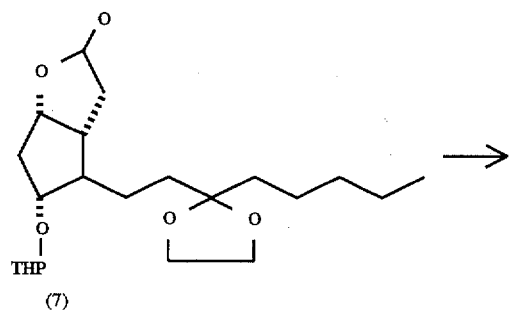
(7)
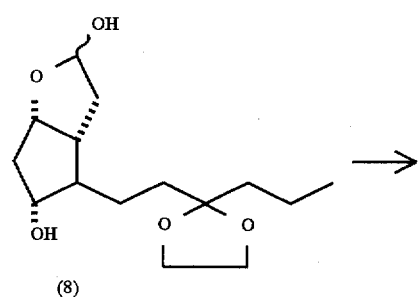
(8)
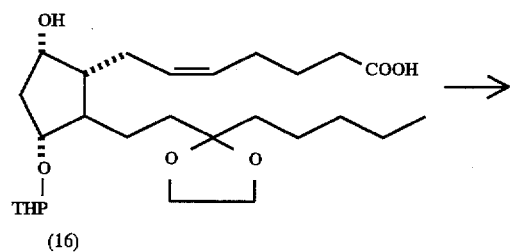
(16)
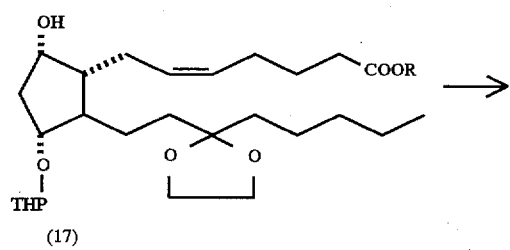
(17)
Synthetic Chart II
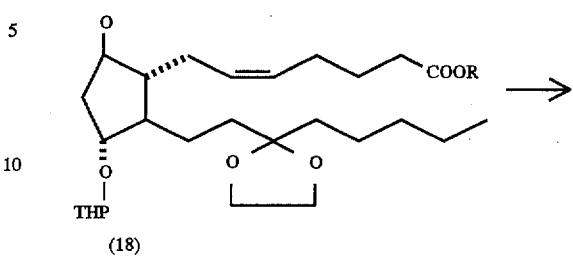
(18)
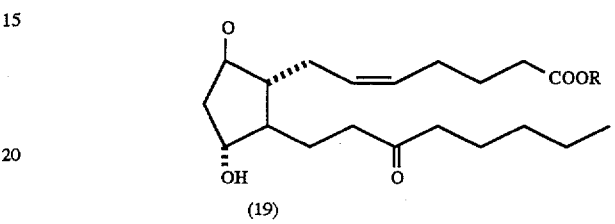
(19)
Synthetic Chart III
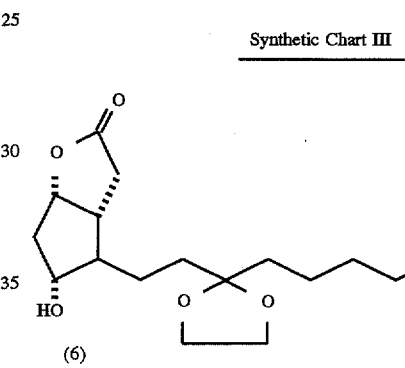
(6)
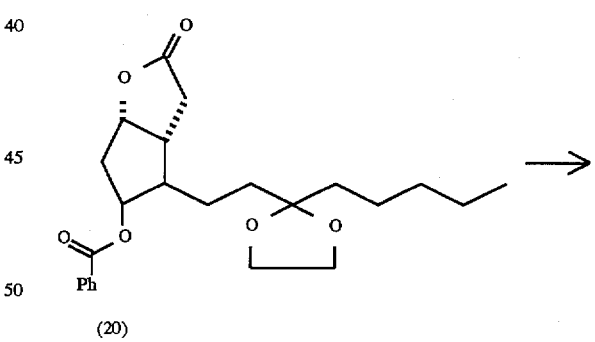
(20)
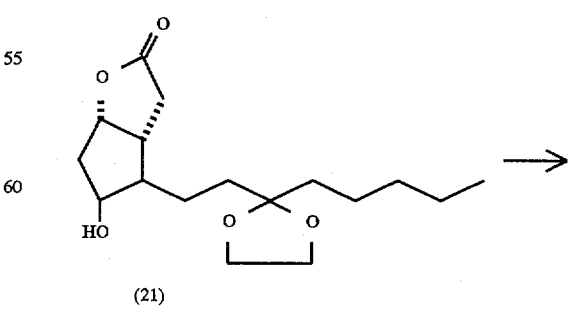
(21)

Synthetic Chart III -continued
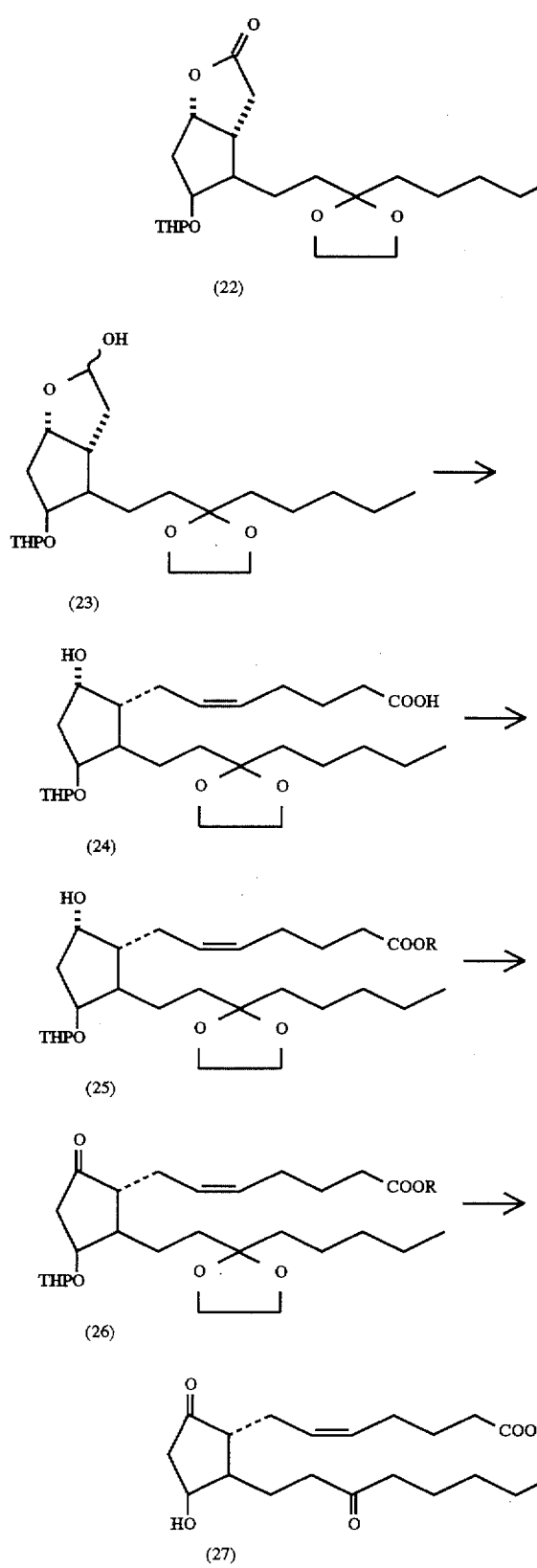
Synthetic Chart IV
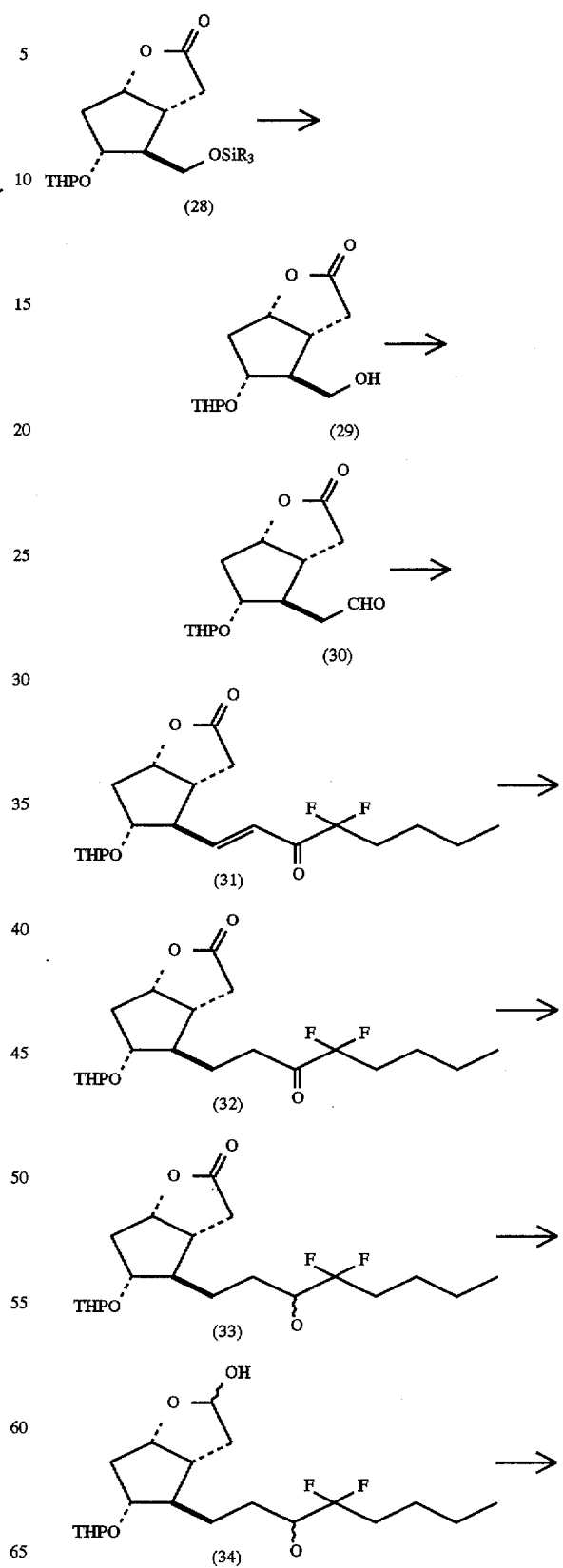

-continued
Synthetic Chart IV
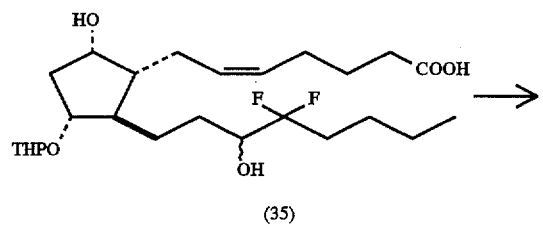
(35)
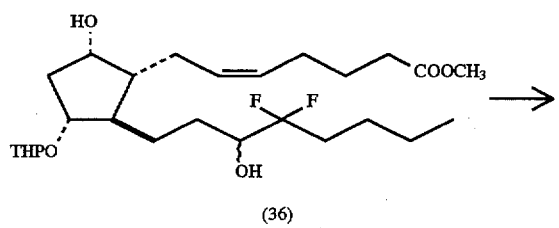
(36)
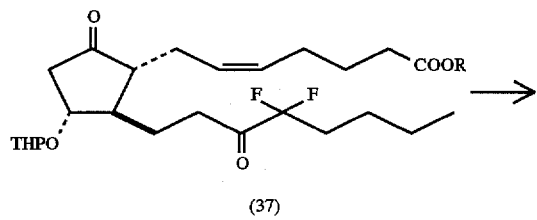
(37)
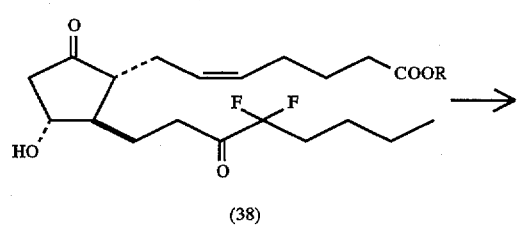
(38)
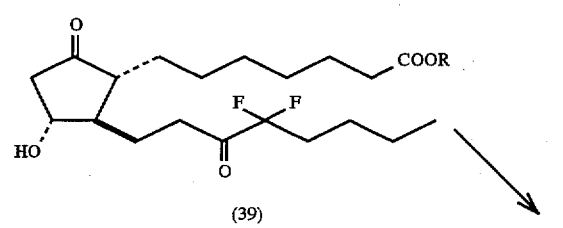
(39)
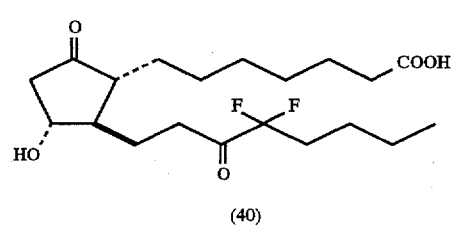
(40)
Synthetic Chart V
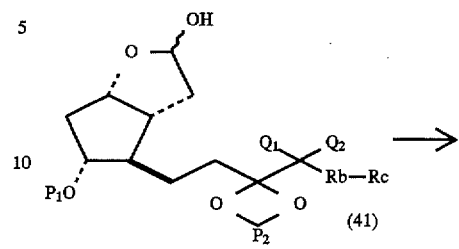
(41)
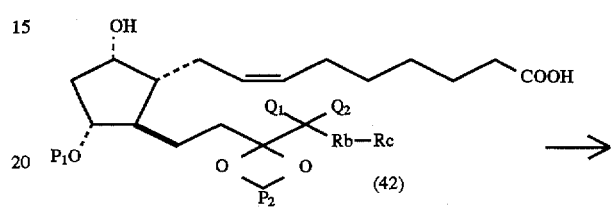
(42)
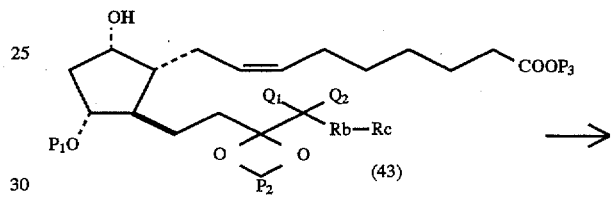
(43)
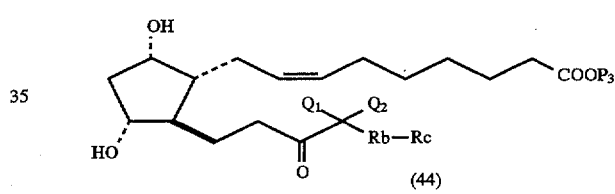
(44)
Synthetic Chart VI
(43) →
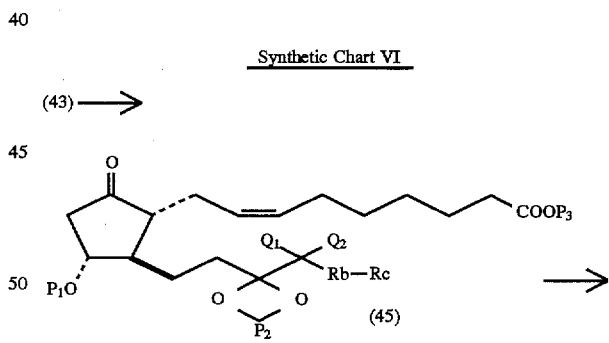
(45)
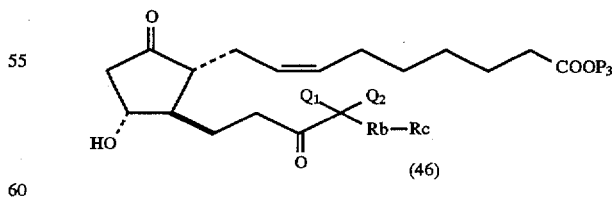
(46)

Synthetic Chart VII
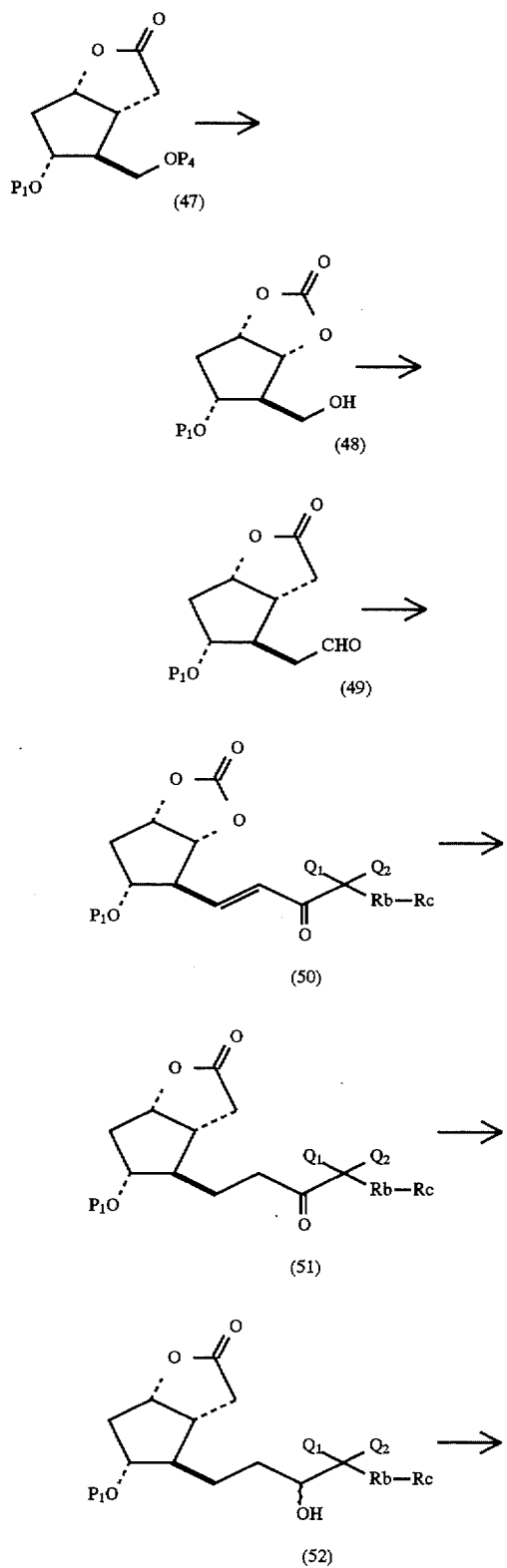
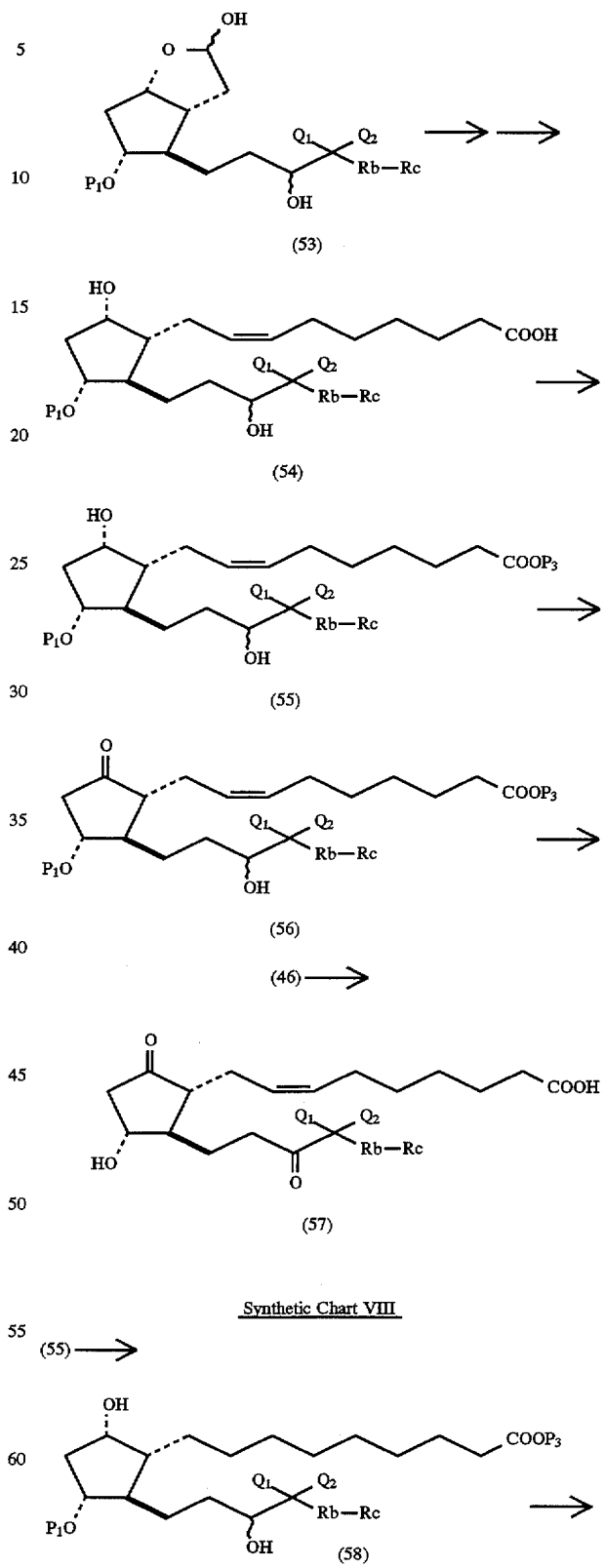
Synthetic Chart VIII
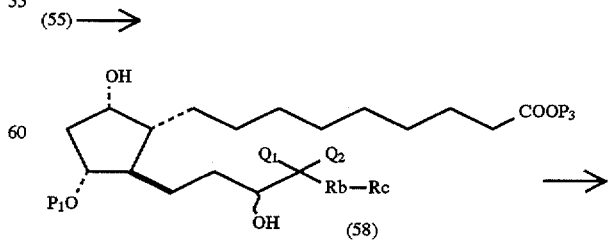

Synthetic Chart VIII
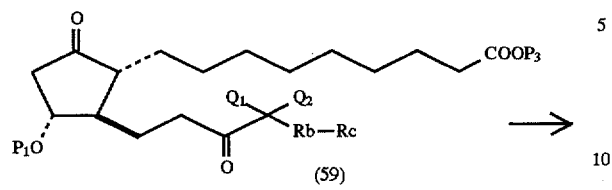
(59)
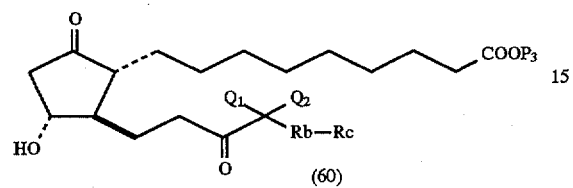
(60)
Synthetic Chart IX
(43) →
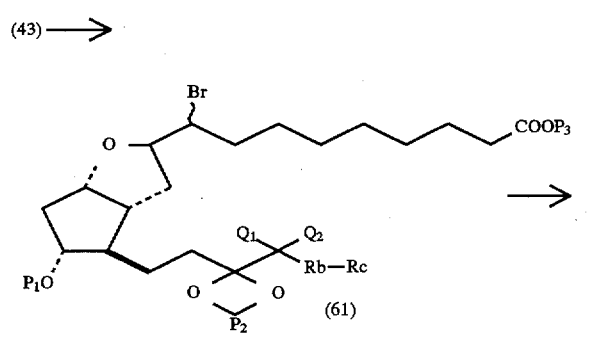
(61)
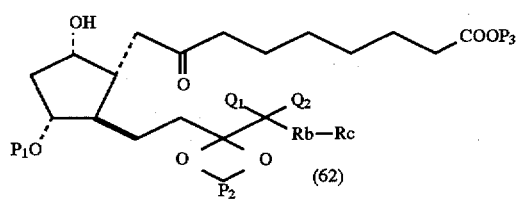
(62)
Synthetic Chart X
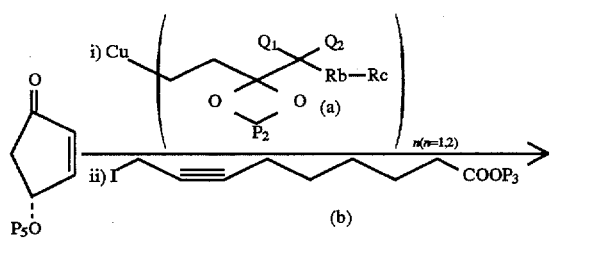
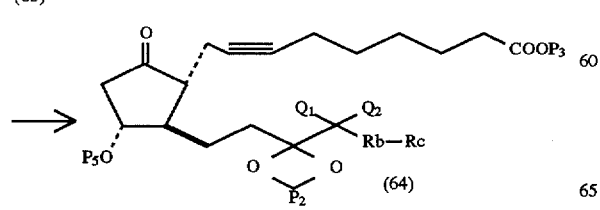
(64)
Synthetic Chart XI
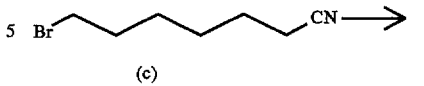
(c)
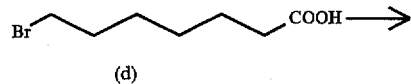
(d)
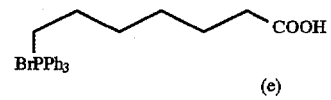
(e)
Synthetic Chart XII
(52) →
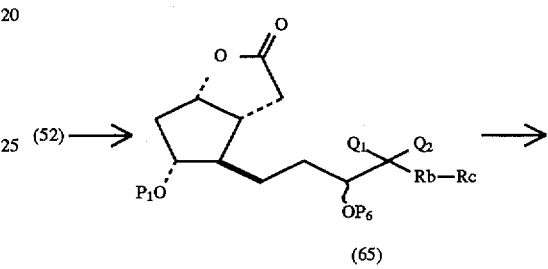
(65)
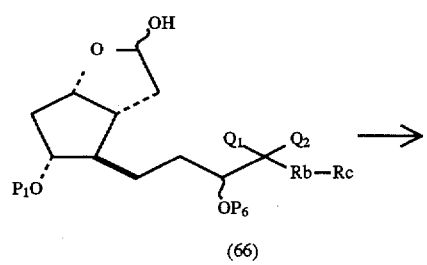
(66)
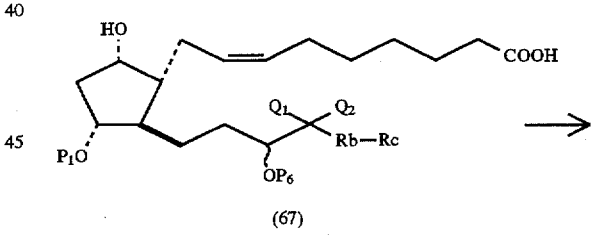
(67)
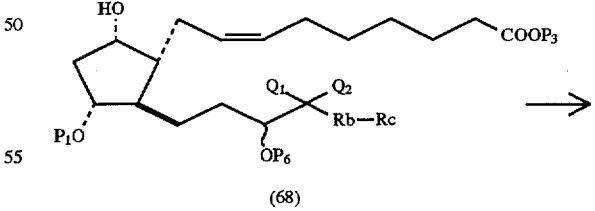
(68)
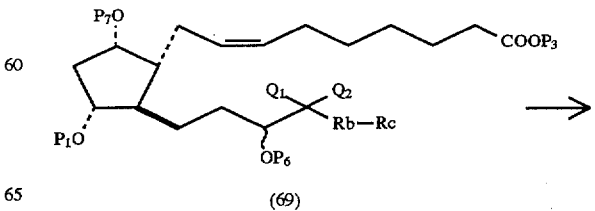
(69)

-continued
Synthetic Chart XII

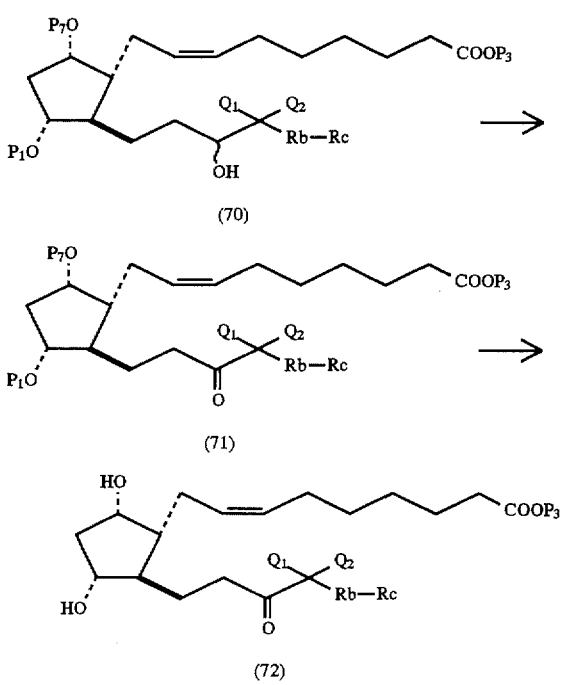

Synthetic Chart XIII

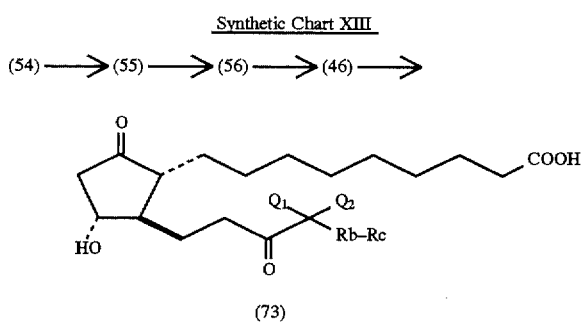

Since the compounds used in the present invention have an activity useful for preventing or curing cataract, these can be used for preparing a medicament for treating cataract. Such activities can be measured by the standard methods such as galactose-induced cataract of rats.

The compounds used in the present invention may be used as a medicine for animals and human beings and usually applied systemically or locally by such methods as ophthalmic administration, oral administration, intravenous injection (including instillation), subcutaneous injection, suppository and the like. While the dosage will vary depending on the particular animal or human patient, age, body weight, symptom to be treated, desired therapeutic effect, administration route, term of treatment and the like, satisfactory effects will be obtained with the dosage of 0.01–100 µg/eye administered locally or 0.001–500 mg/kg administered systemically in 2 to 4 divided doses a day or as a sustained form.

The ophthalmic composition used according to the invention includes ophthalmic solution, ophthalmic ointment and the like. The ophthalmic solution can be prepared by dissolving an active ingredient in a sterile aqueous solution such as a physiological saline or a buffered solution, or as a combination of a solid and a solution for dissolving said solid to make a ready-to-use preparation. The ophthalmic ointment can be prepared by mixing an active ingredient with an ointment base.

The solid composition for oral administration used according to the invention includes tablets, troches, buccals, capsules, pills, powders, granules and the like. The solid composition contains one or more active substances in admixture with at least an inactive diluent, e.g. lactose, mannitol, glucose, hydrocypropyl cellulose, fine crystalline cellulose, starch, polyvinyl pyrolidone, magnesium aluminate metasilicate. The composition may contain additives, in addition to the inactive diluent, for example, lubricants e.g., magnesium stearate, a disintegrator e.g. cellulose calcium gluconates, stabilizers e.g. α-, β- or γ-cyclodextrins, etherated cyclodextrins (e.g. dimethyl-α-, dimethyl-β-, trimethyl-β-, or hydroxypropyl-β-cyclodextrins), branched cyclodextrins (e.g. glucosyl- or maltosyl-cyclodextrins), formyl cyclodextrins, sulfur-containing cyclodextrins, misoprotols or phospholipids. Such cyclodextrins may increase the stability of the compounds by forming an inclusion compounds. The stability may be often increased by forming lyposome with phospholipids. Tablets and pills may be coated with an enteric or gastroenteric film e.g. white sugar, gelatin, hydroxypropylcellulose, hydroxypropylmethylcellulose phthalates and the like, if necessary, and furthermore they may be covered with two or more layers. Additionally, the composition may be in the form of capsules made of substance easily absorbed e.g. gelatin. The composition may be in the form of buccals, when an immediate effect is desired. For this purpose, base e.g. glycerine, lactose may be used.

Liquid compositions for oral administration include pharmaceutically acceptable emulsions, solutions, suspensions, syrups, elixirs and the like and contain a commonly used inactive diluent e.g. purified water or ethyl alcohol. The composition may contain additives e.g. wetting agents, suspending agents, sweeteners, flavors, perfumes and preservatives.

The composition of the present invention may be in the form of sprays which may contain one or more active ingredients and which can be prepared according to a well known methods.

An injection of this invention for non-oral administration includes sterile aqueous or nonaqueous solutions, suspensions, and emulsions. Diluents for the aqueous solution or suspension include, for example, distilled water for injection, physiological saline and Ringer's solution. Diluents for the nonaqueous solution and suspension include, for example, propylene glycol, polyethylene glycol, vegetable oils e.g. olive oil, alcohols, e.g. ethanol and polysorbates. The composition may contain other additives, e.g. preservatives, wetting agents, emulsifying agents, dispersing agents and the like. These are sterilized by filtration through, e.g. a bacteria-retaining filter, compounding with a sterilizer, gas sterilization or radiation sterilization. These can be prepared by producing a sterilized water or a sterilized solvent for injection before use.

Another formulation according to the present invention is a rectal or vaginal suppository. This can be prepared by mixing at least one active compound according to the invention with a suppository base e.g. cacao butter and optionally containing nonionic surfactant for improving absorption.

A more complete understanding of the present invention can be obtained by reference to the following Preparation Examples, Formulation Examples and Test Examples which are provided herein for purpose of illustration only and are not intended to limit the scope of the invention.

PREPARATION EXAMPLE 1

Preparation of 16,16-difluoro-13,14-dihydro-15-keto-PGE$_1$ methyl ester (39)

1-1) Preparation of (1S,5R,6R,7R)-6-hydroxymethyl-7-tetrahydropyranyloxy-2-oxabicyclo[3.3.0]octan-3-one (29)

To a solution of (–) commercial Corey lactone (THP-form, 37.9 g) in tetrahydrofuran was added a solution (1.0M, 300 ml) of tetrabutylammonium fluoride in tetrahydrofuran and the resultant mixture was stirred at room temperature for 3 hours.

Then the resultant mixture was concentrated under reduced pressure and the residue was subjected to column chromatography to give the titled compound (29). Yield: 21.70 g (82.8%).

1-2) Preparation of (1S,5R,6R,7R)-6-{(E)-4,4-difluoro-5-oxo-2-octenyl}-7-tetrahydropyranyloxy-2-oxabicyclo[3.3.0]octan-3-one (31)

A solution (2.0M, 45.5 ml) of oxalyl chloride in methylene chloride was diluted with methylene chloride under an argon atmosphere at –78° C. To this solution was added dropwise dimethylsulfoxide (12.9 ml) and the resultant mixture was stirred for 10 minutes. A solution (1S,5R,6R,7R)-6-hydroxymethyl-7-tetrahydropyranyloxy-2-oxabicylo[3.3.0]octan-3-one (29) (11.65 g) in methylene chloride was added dropwise and the mixture was stirred for 30 minutes. Then triethylamine (56 ml) was added dropwise and stirring was continued for further 1 hour. The resultant mixture was worked up with the conventional procedure to give the crude aldehyde product (30).

To a solution of thallium ethoxide (3.26 ml) in methylene chloride was added under an argon atmosphere dimethyl 3,3-difluoro-2-oxoheptylphosphonate (11.9 g) and the resultant mixture was stirred for 1 hour. After cooling the solution to 0° C., a solution of the aldehyde (30) obtained above in methylene chloride was added dropwise to said solution and the mixture was stirred at room temperature for 14 hours. The reaction mixture was treated with acetic acid, celite and a saturated aqueous potassium idodide solution and filtered. The filtrate was worked up with the conventional procedure and the crude product was subjected to column chromatography to give the titled compound (31). Yield: 7.787 g (44.3%).

1-3) Preparation of (1S,5R,6R,7R)-6-(4,4-difluoro-5-oxooctyl)-7-tetrahydropyranyloxy-2-oxabicyclo[3.3.0]octan-3-one (32)

To a solution of (1S,5R,6R,7R)-6-{(E)-4,4-difluoro-5-oxo-2-octenyl}-7-tetrahydropyranyloxy-2-oxabicyclo[3.3.0]octan-3-one (31) (5.57 g) in ethyl acetate was added 5% Pd/C (catalytic amount) and the resultant mixture was shaken under a hydrogen atmosphere at room temperature for 7 hours. The resultant mixture was filtered and the filtrate was concentrated under reduced pressure to give the titled compound (32) as a crude product. Yield: 5.48 g (97.8%).

1-4) Preparation of (1S,5R,6R,7R)-6-{4,4-difluoro-5(RS)-hydroxyoctyl}-7-tetrahydropyranyloxy-2-oxabicyclo[3.3.0]-octan-3-one (33)

To a solution of (1S,5R,6R,7R)-6-(4,4-difluoro-5-oxooctyl)-7-tetrahydropyranyloxy-2-oxabicyclo[3.3.0]octan-3-one one (32) (5.48 g) in methanol was added sodium borohydride (0.800 g) at 0° C. and the resultant mixture was stirred for 10 minutes. The resultant mixture was worked up with the conventional procedure and the obtained crude product was subjected to column chromatography to give the titled compound (33). Yield: 5.46 g (99.5%).

1-5) Preparation of 16,16-difluoro-13,14-dihydro-11-O-tetrahydropyranyl-PGF$_{2\alpha}$ methyl ester (36)

A solution of (1S,5R,6R,7R)-6-{4,4-dihydro-5(RS)-hydroxyoctyl}-7-tetrahydropyranyloxy-2-oxabicyclo[3.3.0]-octan-3-one (33) (2.579 g) in toluene was cooled to –78° C. under an argon atmosphere. To this solution was added dropwise a solution (1.5M, 9.6 ml) of diisobutylalmium hydride in toluene and stirred for 30 minutes. The resultant mixture was worked up with methanol and a saturated aqueous Rochelle salt solution. Then the resultant solution was worked up with the conventional procedure to give the crude lactol product (34).

To a suspension of 4-carboxybutyl triphenyl phosphine bromide (11.72 g) in tetrahydrofuran was added dropwise under an argon atmosphere a solution (1.0M, 52.84 ml) of potassium tert-butoxide in tetrahydrofuran and the resultant mixture was stirred for 20 minutes. The solution was cooled to 0° C. and combined with a solution of lactol (34) in tetrahydrofuran. The resultant mixture was stirred at room temperature for 15 hours and then worked up with the conventional procedure to give the crude carboxylic acid product (35).

To a solution of the carboxylic acid (35) in acetonitrile was added under an argon atmosphere 1,8-diazabicyclo[5.4.0]undec-7-ene (DBU) (4.0 ml) and methyl iodide (1.7 ml) and the resultant solution was stirred at 60° C. for 30 hours. The resultant solution was worked up with the conventional procedure and the residue was subjected to column chromatography to give the titled compound (36). Yield: 2.737 g (84.5%).

1-6) Preparation of 16,16-difluoro-13,14-dihydro-15-keto-11-O-tetrahydropyranyl-PGE$_2$ methyl ester (37)

To a solution of Collins reagent, prepared from cromic anhydride (16.18 g) and pyridine (26.2 ml) in the conventional process, in methylene chloride was added a solution of 16,16-difluoro-13,14-dihydro-11-O-tetrahydropyranyl-PGF$_{2\alpha}$ methyl ester (36) (2.646 g) in methylene chloride under an argon atmosphere at –20° C. The resultant mixture was stirred at the same temperature for 2 hours and at –5° C. for 9 hours. The solution was treated with ether and sodium hydrogen sulfate and filtered. The filtrate was concentrated under reduced pressure and the residue was subjected to column chromatography to give the titled compound (37). Yield: 1.890 g (64.4%).

1-7) Preparation of 16,16-difluoro-13,14-dihydro-15-keto-PGE$_2$ methyl ester (38)

Into a mixed solvent of acetic acid:water:tetrahydrofuran (3:1:1) was dissolved 16,16-difluoro-13,14-dihydro-15-keto-11-O-tetrahydroxypyranyl-PGE$_2$ methyl ester (37) (2.809 g) and the resultant solution was stirred at 60° C. for 5 hours. The resultant mixture was concentrated under reduced pressure and the residue was subjected to chromatography to give the titled compound (38). Yield: 1.755 g (75.5%).

1-8) Preparation of 16,16-difluoro-13,14-dihydro-15-keto-PGE$_1$ methyl ester (39)

To a solution of 16,16-difluoro-13,14-dihydro-15-keto-PGE$_2$ methyl ester (38) (1.755 g) in ethyl acetate was added Pd/C (catalytic amount) and the mixture was shaken under a hydrogen atmosphere at room temperature for 6 hours. The resultant mixture was filtered. The filtrate was concentrated and the residue was subjected to column chromatography to give the titled compound (39). Yield: 1.655 g (93.8%).

$^1$H NMR (CDCl$_3$) δ0.87(3H,t,J=7 Hz), 1.15–2.05(23H, m), 2.11–2.30(3H,m), 2.50(1H,dd,J=7.5 and 17 Hz), 3.10–3.20 (1H,br), 3.71(3H,s), 4.05–4.20(1H,m) MS(DI-EI) m/z 404(M$^+$), 355 (M$^+$—H$_2$O—CH$_3$O), 297(M$^{+-C}$$_5$H$_9$F$_2$)

PREPARATION EXAMPLE 2

Preparation of 16,16-difluoro-13,14-dihydro-15-keto-$PGE_1$ (40)

2-1) Preparation of (15RS)-16,16-difluoro-13,14-dihydro-11-O-tetrahydropyranyl-$PGF_{2\alpha}$ benzyl ester (36)

To a solution of 16,16-difluoro-13,14-dihydro-11-O-tetrahydropyranyl-$PGF_{2\alpha}$ (35) (2.33 g) in dichloromethane (300 ml) were added DBU (2.1 ml) and benzyl bromide (2.2 ml) and the resultant mixture was stirred at room temperature for 1.5 hour. The resultant mixture was worked up with the conventional procedure and the residue was subjected to silicagel column chromatography to give the titled compound (36). Yield: 2.522 g (96.1%).

2-2) Preparation of 16,16-difluoro-13,14-dihydro-15-keto-11-O-tetrahydropyranyl-$PGE_2$ benzyl ester (37)

Collins reagent was prepared by using chromic anhydride (13.5 g) and pyridine (21.8 ml) in dichloromethane (300 ml), and to this were added Celite (40 g) and (15RS)-16,16-difluoro-13,14-dihydro-11-O-tetrahydropyranyl-$PGF_{2\alpha}$ benzyl ester (36) (2.550 g). The resultant mixture was worked up with the conventional procedure and the residue was subjected to silicagel column chromatography to give the titled compound (37). Yield: 1.991 g (78.6%).

2-3) Preparation of 16,16-difluoro-13,14-dihydro-15-keto-$PGE_2$ benzyl ester (38)

Into a mixed solvent of acetic acid:THF:water (3:1:1, 50 ml) was dissolved 16,16-difluoro-13,14-dihydro-15-keto-11-O-tetrahydropyranyl-$PGE_2$ benzyl ester (37) (1.550 g) and the solution was kept at 50° C. for 4 hours. The resultant mixture was worked up with the conventional procedure and the residue was subjected to silicagel column chromatography to give the titled compound (38). Yield: 1.225 g (92.9%).

2-4) Preparation of 16,16-difluoro-13,14-dihydro-15-keto-$PGE_1$ (40)

To a solution of 16,16-difluoro-13,14-dihydro-15-keto-$PGE_1$ benzyl ester (38) (0.844 g) in ethyl acetate (30 ml) was added 5% Pd/C and the mixture was shaken under a hydrogen atmosphere. The resultant mixture was worked up with the conventional procedure and the residue was subjected to silicagel column chromatography to give the titled compound (43). Yield: 0.404 g.

$^1$H NMR ($CDCl_3$) δ0.94 (t,3H,J=7.5 Hz), 1.20–2.70 (m,26H), 4.19 (m,1H), 4.80 (br,2H). MS(DI-EI) m/z 390 ($M^+$), 372($M^+$—$H_2O$), 354($M^+$—$2H_2O$)

PREPARATION EXAMPLE 3

Preparation of 20-ethyl-2-decarboxy-2-(2-carboxyethyl)-13,14-dihydro-15-keto-$PGF_{2\alpha}$ isopropyl ester (44) [IUPAC nomenclature: isopropyl (Z)-9-(1R)-[(2R,3R,5S)-3,5-dihydroxy-2-(3-oxodecyl)cyclopentyl]-7-nonenoate]

3-1) Preparation of (Z)-9-(1R)-[(2R,3R,5S)-2-(3,3-ethylenedioxydecyl)-5-hydroxy-5-hydroxy-3-(tetrahydropyranyloxy)cyclopentyl]-7-nonenoic acid (42)

Sodium hydride (60%, 0.422 g) was washed with hexane under an argon atmosphere. To this was added dimethyl sulfoxide (DMSO, 10 ml) and the resultant mixture was kept at 60° C. for 3 hours. After cooling to the room temperature, the resultant mixture was treated with 6-carboxyhexyltriphenylphosphonium bromide (2.49 g), stirred at the room temperature for 2 hours, then at 45° C. for 1 hour, and poured into ice-water. The resultant mixture was worked up with the conventional procedure to give the titled compound (42). Yield: 1.68 g.

3-2) Preparation of isopropyl (Z)-9-(1R)-[(2R,3R,5S)-2-(3,3-ethylenedioxydecyl)-5-hydroxy-3-(tetrahydropyranyloxy)cyclopentyl]-7-nonenoate (43)

The compound (42) (1.68 g) was esterified in the conventional procedure with 1,8-diazabicyclo[5.4.0]-7-undecene (DBU, 0.78 ml) and isopropyl iodide (0.35 ml) in acetonitrile (15 ml). The residue was subjected to silicagel column chromatography to give the titled compound (43). Yield: 0.908 g (88%)

3-3) Preparation of isopropyl (Z)-9-(1R)-[(2R,3R,5S)-3,5-dihydroxy-2-(3-oxodecyl)cyclopentyl]-7-nonenoate (44)

The compound (43) (0.305 g) was dissolved in a mixed solvent (6 ml) consisting of acetic acid, THF and water (2:1:1) and kept at 50° C. for 14 hours. The resultant mixture was worked up with the conventional procedure and the obtained crude product was subjected to silicagel column chromatography to give the titled compound (44). Yield: 0.213 g (90%).

Compound (44) [$Q_1=Q_2$=H, Rb-Rc=hexyl, $P_3$=isopropyl] NMR ($CDCl_3$) δ: 0.85 (t,3H,J=6.5 Hz), 1.20 (d,6H,J=6 Hz), 1.23–2.65 (m,34H), 3.86 (m,1H), 4.16 (m.1H), 4.99 (Hept,1H,J=6 Hz), 5.39 (m,2H)

PREPARATION EXAMPLE 4

Preparation of 20-ethyl-2-decarboxy-2-(2-carboxyethyl)-13,14-dihydro-15-keto-$PGE_2$ isopropyl ester (46) [IUPAC nomenclature: isopropyl (Z)-9-(1R)-[(2R,3R)-3-hydroxy-5-oxo-2-(3-oxodecyl)cyclopentyl]-7-nonenoate]

4-1) Preparation of (Z)-9-(1R)-[(2R,3R)-2-(3,3-ethylenedioxydecyl)-5-oxo-3-(tetrahydropyranyloxy)cyclopentyl]-7-nonenoate (45)

Oxalyl chloride (2M, 0.45 ml) and DMSO (0.13 ml) were added to dichloromethane (5 ml) cooled previously to −70° C. and the resultant mixture was stirred for 15 hours. A solution of isopropyl (Z)-9-(1R)-[(2R,3R,5S)-2-(3,3-ethylenedioxydecyl)-5-hydroxy-(3-tetrahydropyranyloxy)cyclopentyl]-7-nonenoate (43) (0.35 g) in dichloromethane (7 ml) was added dropwise to the above solution. After stirring at −55° C. for 15 minutes, the resultant mixture was treated with triethylamine (0.25 ml) and warmed up to 10° C. over 6 hours. The resultant mixture was worked up with the conventional procedure and the obtained crude product was subjected to silicagel column chromatography to give the titled compound (45). Yield: 0.311 g (89%).

4-2) Preparation of isopropyl (Z)-9-(1R)-[(2R,3R)-3-hydroxy-5-oxo-2-(3-oxodecyl)cyclopentyl]-7-nonenoate (46)

The compound (45) (0.311 g) was dissolved in a mixed solvent (5 ml) consisting of acetic acid, THF and water (2:1:1) and kept at 50° C. for 3 hours. The resultant mixture was worked up with the conventional procedure and the residue was subjected to silicagel column chromatography to give the titled compound (46). Yield: 0.156 g (66%).

Compound (46) [$Q_1=Q_2$=H, Rb-Rc=hexyl, $P_3$=isopropyl] NMR ($CDCl_3$)δ: 0.86 (t,3H,J=6.5 Hz), 1.20 (d,6H,J=6 Hz), 1.23–2.75 (m,33H), 4.20 (m,1H), 4.99 (Hept,1H,J=6 Hz), 5.15–5.50 (m,2H)

PREPARATION EXAMPLE 5

Preparation of 2-decarboxy-2-(2-carboxyethyl)-13,14-dihydro-16,16-difluoro-15-keto-$PGE_2$ (47) [IUPAC nomenclature: (Z)-9-(1R)-[(2R,3R)-2-(4,4-difluoro-3-oxooctyl)-3-hydroxy-5-oxopentyl]-7-nonenoic acid]

Preparation of starting compound: (6-carboxyhexyl)triphenylphosphonium bromide (e).

A mixture of 7-bromoheptanonitrile (c) (10.0 g) and 40% hydrobromic acid (80 ml) was heated under reflux for 6 hours. The mixture was diluted with water, extracted with ether and then worked up with the conventional procedure to give a crude product. The residue was subjected to silicagel column chromatography to give 7-bromoheptanoic acid (d). Yield: 7.60 g (69%)

Treatment of 7-bromoheptanoic acid (d) (7.60 g) with triphenylphosphine (10.0 g) gave (6-carboxyhexyl) triphenylphosphonium bromide (e). Yield: 16.0 g (93%). Preparation of the desired compound 5-1) Preparation of (1S,5R,6R,7R)-6-(4,4-difluoro-3-oxooctenyl)-7-(tetrahydropyranyloxy)-2-oxabicyclo[3.3.0]octan-3-one (50)

The Swern oxidation of (1S,5R,6R,7R)-6-hydroxymethyl-7-(tetrahydropyranyloxy)-2-oxabicyclo[3.3.0]octan-3-one (48) (27.8 g), which was obtained from commercial (1S,5R,6R,7R)-6-(5-butyldimethylsilyloxymethyl)-7-(tetrahydropyranyloxy)-2-oxabicyclo[3.3.0]octan-3-one (47), using oxalyl chloride (2.0M, 109.3 ml), DMSO (31.0 ml) and trimethylamine (150 ml) in dichloromethane (800 ml) gave the compound (49) ($P_1$=tetrahydropyranyl).

The above compound (49) was reacted with dimethyl 3,3-difluoro-2-oxoheptylphosphonate (30.0 g) in dichloromethane in the presence of thallium methoxide (8.23 ml). The resultant mixture was worked up with the conventional procedure and the obtained crude product was subjeced to silicagel column chromatography to give the titled compound (50). Yield: 24.4 g (58%).

5-2) Preparation of (1S,5R,6R,7R)-6-(4,4-difluoro-3-oxooctyl)-7-tetrahydropyranyloxy-2-oxabicyclo[3.3.0]octan-3-one (51)

The compound (50) (12.7 g) was catalytically hydrogenated over 5% palladium on carbon (catalytic amount) in ethyl acetate (300 ml) under hydrogen atmosphere to give the titled compound (51). Yield: 12.5 g (99%).

5-3) Preparation of (1S,5R,6R,7R)-6-[4,4-difluoro-3(R,S)-hydroxyoctyl]-7-tetrahydroxypyranyloxy)-2-oxabicyclo[3.3.0]octan-3-one (52)

The compound (51) (12.6 g) was reduced with sodium borohydride (1.25 g) in methanol (400 ml) at 0° C. to give the titled compound (52). Yield: 12.1 g (95.5%).

5-4) Preparation of (1S,5R,6R,7R)-6-[4,4-difluoro-3(R,S)-hydroxyoctyl]-7-tetrahydroxypyranyloxy)-2-oxabicyclo[3.3.01]octan-3(R,S)-ol (53)

The compound (52) (12.1 g) was reduced with diisobutylaluminum hydride (1.5M, 65.1 ml) in toluene (500 ml) at −78° C. and the obtained crude product was subjected to silicagel column chromatography to give the titled compound (53). Yield: 11.1 g (91%).

5-5) Preparation of phenacyl (Z)-9-(1R)-[(2R,3R,5S)-2-{4,4-difluoro-(3RS)-hydroxyoctyl}-5-hydroxy-3-(tetrahydropyranyloxy)cyclopentyl]-7-nonenoate (55)

Sodium hydride (60%, 1.63 g) was washed with pentane. To this was added DMSO (40 ml) and the resultant mixture was kept at 65°–70° C. for 1.5 hours. After cooling to the room temperature, carboxyhexylphosphonium bromide (e) (9.61 g) was added to the mixture to form a ylid. A solution of the compound (53) in DMSO (15 ml) was added dropwise to the ylid in solution and the mixture was kept overnight at the room temperature. The resultant mixture was worked up with conventional procedure to give the. compound (54). Yield: 3.18 g (crude).

The compound (54) (0.795 g), phenacyl bromide (1.01 g) and diisopropylethylamine (0.89 ml) were dissolved in acetonitrile (10 ml) and the solution was kept at the room temperature for 20 minutes and then at 45° C. for 30 minutes. The resultant mixture was worked up with the conventional procedure and the obtained crude product was subjected to silicagel column chromatography to give the titled compound (55). Yield: 0.604 g.

5-6) Preparation of phenacyl (Z)-9-(1R)-[(2R,3R)-2-{4,4-difluoro-3-oxooctyl}-5-oxo-3-(tetrahydropyranyloxy)cyclopentyl]-7-nonenoate (56)

DMSO (0.92 ml) was added dropwise to a solution, cooled to −78° C., of oxalyl chloride 0.52 ml) in dichloromethane (30 ml). The compound (55) (0.609 g) dissolved in dichloromethane (15 ml) was added to the above solution and the resultant mixture was stirred at −30° C. to −20° C. for 1.5 hours. The resultant mixture was treated with triethylamine (1.88 ml) and stirred for 30 minutes. The resultant mixture was worked up with the conventional procedure and the obtained crude product was subjected to silicagel column chromatography to give the titled compound (56). Yield: 0.514 g (85%).

5-7) Preparation of phenacyl (Z)-9-(1R)-[(2R,3R)-2-{4,4-difluoro-3-oxooctyl}-3-hydroxy-5-oxocyclopentyl]-7-nonenoate (46)

The compound (56) (0.514 g) was dissolved in a mixed solvent (30 ml) consisting of acetic acid, THF and water (4:2:1) and the solution was kept overnight at the room temperature. The resultant mixture was worked up with the conventional procedure and the obtained crude product was subjected to silicagel column chromatography to give the titled compound (46). Yield: 0.272 g (61%).

Compound (46) [$Q_1$=$Q_2$=F, Rb-Rc=butyl, $P_3$=phenacyl]
NMR (CDCl$_3$) δ: 0.92 (t,3H,J=7.5 Hz), 1.2–2.9 (m,27H), 4.18 (m,1H), 5.4 (m,2H), 7.4–8.0 (m,5H)

5-8) Preparation of (Z)-9-(1R)-[(2R,3R)-2-(4,4-difluoro-3-oxooctyl)-3-hydroxy-5-oxocyclopentyl]-7-nonenoic acid (57)

A solution of the compound (46) (0.272 g) in acetic acid (10 ml) was treated with zinc (3.5 g) added in portions at the room temperature for 2.5 hours. The resultant mixture was worked up with the conventional procedure and the residue was subjected to silicagel column chromatography to give the titled compound (57). Yield: 0.177 g (81%).

Compound (57) [$Q_1$=$Q_2$=F, Rb-Rc=butyl]
NMR (CDCl$_3$)δ: 0.93 (t,3H,J=6.5 Hz), 1.15–2.95 (m,28H), 4.19 (m,1H), 5.36 (m,1H)

PREPARATION EXAMPLE 6

Preparation of 2-decarboxy-2-(2-carboxyethyl)-13,14-dihydro-16,16-difluoro-15-keto-PGE$_1$ isopropyl ester [IUPAC nomenclature: isopropyl 9-(1R)-[(2R,3R)-2-(4,4-difluoro-3-oxooctyl)-3-hydroxy-5-oxocyclopentyl] nonanoate 6-1) Preparation of isopropyl (Z)-9-(1R)-[(2R,3R,5S)-2-{4,4-difluoro-(3RS)-hydroxyoctyl}-5-hydroxy-3-(tetrahydropyranyloxy)cyclopentyl]-7-nonenoate (55)

The compound (54) (0.802 g) obtained in Preparation Example 5, DBU (0.76 ml) and isopropyl iodide (0.51 ml) were dissolved in acetonitrile (15 ml) and kept at 50° C. for 1 hour. Further the compound (54) (0.492 g) was treated in the same way. The resultant mixture was worked up with the conventional procedure to give the titled compound (55). Yield (combined): 0.315 g.

6-2) Preparation of isopropyl 9-(1R)-[(2R,3R)-2-{4,4-difluoro-(3RS)-hydroxyoctyl}-5-hydroxy-3-(tetrahydropyranyloxy)cyclopentyl]-7-nonanoate (58)

The compound (55) (0.315 g) was catalytically hydrogenated over palladium on carbon (5%, 0.08 g) in ethanol (20 ml) under hydrogen atmosphere to give the titled compound (58). Yield: 0.301 g (95%)

6-3) Preparation of isopropyl 9-(1R)-[(2R,3R)-2-(4,4-difluoro-3-oxooctyl}-5-oxo-3-(tetrahydropyranyloxy)cyclopentyl]nonanoate (59)

The compound (58) (0.301 g) was subjected to Swern oxidation using oxalyl chloride (0.34 ml), DMSO (0.61 ml)

and triethylamine (1.22 ml) in dichloromethane to give the entitled compound (59). Yield: 0.288 g (96%).

6-4) Preparation of isopropyl 9-(1R)-[(2R,3R)-2-(4,4-difluoro-3-oxooctyl}-3-hydroxy-5-oxocyclopentyl] nonanoate (60)

The compound (59) (0.288 g) was dissolved in a mixed solvent (30 ml) consisting of acetic acid, water and THF (4:2:1) and the solution was kept at 45° C. for 3.5 hours. The resultant mixture was worked up with the conventional procedure and the obtained crude product was subjected to silicagel column chromatography to give the titled compound (60). Yield: 0.184 g (76%).

Compound (60) [$Q_1=Q_2=F$, Rb-Rc=butyl, $P_3$=isopropyl]

NMR (CDCl$_3$) δ: 0.94 (t,3H,J=6.5 Hz), 1.24 (d,6H,J=6 Hz), 1.27–2.95 (m,31H), 4.19 (m,1H), 5.02 (Hept, 1H,J=6 Hz)

The compounds of the formula I wherein D is —CO—CH$_2$— and those wherein D is —C≡C— can be prepared as follows:

PREPARATION EXAMPLE 7

Preparation of 2-decarboxy-2-(2-carboxyethyl)-13,14-dihydro-6,15-diketo-PGF$_{1\alpha}$ isopropyl ester The compound (43) obtained in Preparation Example 3 is dissolved in a mixture of anhydrous tetrahydrofuran and anhydrous methylenechloride. A small excess amount of N-bromosuccinimide is added to the solution at 0° C. and the resultant mixture is stirred for 5 minutes. The resultant mixture is worked up with the conventional procedure and the crude product is subjected to column chromatography to give the compound (61) ($Q_1=Q_2=H$, Rb-Rc=butyl, $P_1$=tetrahydroxypyranyl, $P_2$=ethylene, $P_3$=isopropyl). This is dissolved in anhydrous toluene. The solution is treated with DBU and stirred overnight at 40° C. After cooling with ice, the solution is acidified with N-HCl, stirred for 10 minutes and extracted with ethyl acetate. The resultant mixture is worked up with the conventional procedure and the residue is subjected to column chromatography to give the compound (62) (symbols having the same meaning as above). Removal of the protective groups in a manner similar to that in the step 3-3) in Preparation Example 3 gives the titled compound.

PREPARATION EXAMPLE 8

Preparation of 2-decarboxy-2-(2-carboxyethyl)-5,6-dehydro-13,14-dihydro-15-keto-PGE$_2$ methyl ester Tert-butyl lithium is added dropwise to a solution of 8-methoxy-3,3-ethylenedioxy-1-iodooctane (prepared according to JP-A-52753/1989) in ether at −78° C. over 30 minutes and the resultant mixture is stirred for 3 hours. Then a solution, cooled to −78° C., of cuprous iodide and tributylphosphine in ether is added to the above mixture in one portion and the resultant mixture is stirred for 20 minutes to form the complex (a). A solution of 4R-tert-butyldimethylsililoxy-2-cyclopenten-1-one (63) in tetrahydrofuran is added dropwise to the mixture over 95 minutes. The resultant mixture is stirred for 15 minutes and transferred to a cooling bath at −30° C. A solution of 8-methoxycarbonyl-1-iodooctyne (b) in HMPA is added to the cooled mixture, which is then stirred for 4.5 hours. Stirring is continued at the room temperature for 12 hours and then the mixture is poured into an aqueous ammonium chloride. The organic layer is separated and worked up with the conventional procedure to give a crude product. The crude product is subjected to column chromatography to give the compound (64) [$Q_1=Q_2=H$, Rb-Rc=butyl, $P_3$=methyl, $P_5$=tert-butyldimethylsilyl]. Deprotection of this in the conventional manner gives the titled compound.

PREPARATION EXAMPLE 9

Preparation of 2-decarboxy-2-(2-carboxyethyl)-13,14-dihydro-16,16-difluoro-15-keto-PGF$_2$ methyl ester (72) [IUPAC nomenclature: methyl (Z)-9-(1R)-[(2R,3R,5S)-2-(4,4-difluoro-3-oxooctyl)-3,5-dihydroxcyclopentyl]-7-nonennoate 9-1) Preparation of (1S,5R,6R,7R)-6-[3(R,S)-t-butyldimethylsilyloxy-4,4-difluorooctyl]-7-(tetrahydropyranyloxy)-2-oxabicyclo[3.3.0]octan-3(R,S)-ol (66)

The compound (52) [$Q_1=Q_2=F$, $P_1$=tetrahydropyranyl, Rb-Rc=butyl] (1.26 g) was treated with imidazole (2.63 g) and tert-butyldimethylsilyl chloride (2.91 g) in DMF (15 ml) to give the silyl ether (65). Yield: 1.43 g (88%).

The silyl ether (65) (1.43 g) was reduced with diisobutylalminum hydride in the conventional procedure to give the titled compound (66). Yield: 1.47 g (100%).

9-2) Preparation of methyl (Z)-9-(1R)-[(2R,3R,5S)-2-{3(R,S)-tert-butyldimethy-4,4-difluorooctyl}-5-hydroxy-3-(tetrahydropyranyloxy)cyclopentyl]-7-nonenoate (68)

A ylid was prepared from sodium hydride (60%, 0.934 g), DMSO (25 ml) and (6-carboxyhexyl)triphenylphosphonium bromide (5.50 g) in the conventional procedure. The ylid was added to a solution of the compound (66) in ether (8 ml) and the resultant mixture was stirred at the room temperature for 2 hours. The resultant mixture was worked with the conventional procedure to give the carboxylic acid (67), which was treated with diazomethane. The product was subjected to silicagel column. chromatography to give the titled compound (68). Yield: 0.43 g (48%).

9-3) Preparation of methyl (Z)-9-(1R)-[(2R,3R,5S)-2{3(R,S)-tert-butyldimethysilyloxy-4,4-difluorooctyl}-3,5-(ditetrahydropyranyloxy)cyclopentyl]-7-nonenoate (69)

The compound (68) (0.438 g) was converted to ditetrahydropyranyl ether using an excess amount of dihydropyran and a catalytic amount of p-toluenesulfonic acid in dichloromethane (25 ml). The resultant mixture was subjected to silicagel column chromatography to give the compound (69). Yield: 0.494 g (99%).

9-4) Preparation of methyl (Z)-9-(1R)-[(2R,3R,5S)-2-(tert-butyldimethylsilyloxy-3-oxooctyl)-3,5-(ditetrahydropyranyloxy)cyclopentyl]-7-nonenoate (71)

The compound (69) (0.494 g) was dissolved in THF (10 ml). Tetrabutylammonium trifluoride (1.0M, 5.6 ml) was added to the solution and the resultant mixture was kept overnight. Then the resultant mixture was worked up with the conventional procedure to give the deprotected compound (70). Yield: 0.284 g (68%).

The compound (70) (0.284 g) was subjected to Swern oxidation using oxalyl chloride (0.165 ml) and DMSO (0.3 ml) in dichloromethane (10 ml). The product was subjected to silicagel column chromatography to give the compound (71). Yield: 0.251 g (89%).

9-5) Preparation of methyl (Z-9-(1R)-[(2R,3R,5S)-2-(4,4-difluoro-3-oxooctyl)-3,5-dihydroxycyclopentyl]-7-nonenoate (72)

The compound (71) was dissolved in a mixed solvent (30 ml)-consisting of acetic acid, water and THF (4:2:1) and the solution was kept at 45° to 50° C. for 3 hours. The resultant mixture was worked up with the conventional procedure and the obtained crude product was subjected to silicagel column chromatography to give the titled compound (72). Yield: 0.137 (76%).

Compound (72) [$Q_1=Q_2=F$, Rb-Rc=butyl, $P_3$=methyl]

NMR (CDCl$_3$) δ: 0.92 (t,3H,J=7.5 Hz), 1.2–2.9 (m,38H), 3.67 (s,3H), 3.70 (q,1H,J=7.5 Hz), 4.25 (m,1H), 5.43 (m,2H)

PREPARATION EXAMPLE 10

Preparation of 2-decarboxy-2-(2-carboxyethyl)-13,14-dihydro-16,16-difluoro-15-keto-PGE$_1$ (73) [IUPAC nomenclature: (Z)-9-(1R)-[(2R,3R,5S)-2-(4,4-difluoro-3-oxooctyl)-3-hydroxy-5-oxocyclopentyl]nonanoic acid]

10-1) Preparation of benzyl (Z)-9-(1R)-[(2R,3R,5S)-3-{4,4-difluoro-3(R,S)-hydroxyoctyl}-5-hydroxy-3-(tetrahydropyranyloxy)cyclopentyl]-7-nonenoate (55)

The compound (54) [Q$_1$=Q$_2$=F, P$_1$=tetrahydropyranyl, Rb-Rc=butyl] (1.09 g) was dissolved in acetonitrile (20 ml) and DBU (2.6 ml) and benzyl bromide (2.2 ml) were added to the solution. The resultant mixture was kept at 45° C. for 1 hour and then overnight at 60° C. The resultant mixture was worked up with the conventional procedure and the obtained crude product was subjected to silicagel column chromatography to give the titled compound (65). Yield: 0.213 g.

10-2) Preparation of benzyl (Z)-9-(1R)-[(2R,3R,5S)-2-(4,4-difluoro-3-oxooctyl-3-tetrahydropyranyloxy)-5-oxocyclopentyl]-7-nonenoate (56)

The compound (55) (0.213 g) was subjected to Swern oxidation using oxalyl chloride (0.23 ml), DMSO (0.41 ml) and triethylamine (0.81 ml) in dichloromethane (15 ml). The product was subjected to silicagel column chromatography to give the titled compound (56). Yield: 0.181 g (86%).

10-3) Preparation of benzyl (Z)-9-(1R)-[(2R,3R,5S)-2-(4,4-difluoro-3-oxooctyl)-3-hydroxy-5-oxocyclopentyl]-7-nonenoate (46)

The compound (56) (0.181 g) was dissolved in a mixed solvent (25 ml) consisting of acetic acid, water and THF (4:2:1) and the solution was kept at 45° C. for 3.5 hours. The resultant mixture was worked up with the conventional procedure and the obtained crude product was subjected to silicagel column chromatography to give the titled compound (46). Yield: 0.140 g (91%).

Compound (46) [Q$_1$=Q$_2$=F, Rb-Rc=butyl, P$_3$=benzyl]

NMR (CDCl$_3$) δ: 0.93 (t,3H,J=7.5 Hz), 1.2–2.8 (m,27H), 4.20 (m,1H), 5.12 (s,2H), 5.2–5.5 (m,2H), 7.35 (m,5H)

10-4) Preparation of 9-(1R)-[(2R,3R,5S)-2-(4,4-difluoro-3-oxooctyl-3-hydroxy-5-oxocyclopentyl]nonanoic acid (73)

The compound (46) was dissolved in ethyl acetate (15 ml). Palladium on carbon (50 mg) was added to the solution and shaken under the hydrogen atmosphere. After removing the catalyst by filtration, the filtrate was concentrated and the produced crude product was subjected to Lobar column (ODS) chromatography to give the titled compound (73). Yield: 0.077 g (65%).

Compound (73) [Q$_1$=Q$_2$=F, Rb-Rc=butyl]

NMR (CDCl$_3$) δ: 0.95 (t,3H,J=7.5 Hz), 1.2–2.8 (m,32H), 4.20(m,1H)

PREPARATION EXAMPLE 11

Preparation of 20-ethyl-2-decarboxy-2-(2-carboxyethyl)-13,14-dihydro-16,16-difluoro-15-keto-PGE$_1$ isopropyl ester (60) [IUPAC nomenclature: isopropyl (Z)-9-(1R)-[(2R,3R)-2-(4,4-difluoro-3-oxodecyl)-3-hydroxy-5-oxocyclopentyl]-7-nonenoate]

The procedure of Preparation Example 6 was repeated except that dimethyl (3,3-difluoro-2-oxononyl)phosphonate was used to give the titled compound (60).

Compound (60) [Q$_1$=Q$_2$=F, Rb-Rc=hexyl, P$_3$=isopropyl]

NMR (CDCl$_3$) δ: 0.90 (t,3H,J=7.5 Hz), 1.32 (d,6H,J=6 Hz), 1.25–2.70 (m,34H), 3.15 (s,1H), 4.20 (m,1H), 5.00 (Hept, 1H,J=7.5 Hz)

PREPARATION EXAMPLE 12

Preparation of 2-decarboxy-2-(2-carboxyethyl)-13,14-dihydro-15-keto-PGE$_2$ isopropyl ester (46) [IUPAC nomenclature: isopropyl (Z)-9-(1R)-[(2R,3R)-2-(3-oxopentyl)-3-hydroxy-5-oxocyclopentyl]-7-nonenoate]

The procedure of Preparation Example 4 was repeated except that dimethyl 2-oxoheptylphosphonate was used to give the titled compound (46).

Compound (46) [Q$_1$=Q$_2$=H, Rb-Rc=butyl, P$_3$=isopropyl]

NMR (CDCl$_3$) δ: 0.89 (t,3H,J=6.6 Hz), 1.18 (d,6H,J=6.2 Hz), 1.15–3.0 (m,29H), 4.04 (m,1H), 4.99 (hept, 1H, J=6.2 Hz), 5.37 (m,2H)

Formulation Example 1

|  | (Parts by weight) |
|---|---|
| 13,14-dihydro-15-keto-16,16-difluoro-PGE$_2$ | 1 |
| mannitol | 5 |
| distilled water | 0.4 |

The above ingredients were mixed, stirred, sterilized, filtered and lyophilized to give powders for injection.

Formulation Example 2

|  | (Parts by weight) |
|---|---|
| 13,14-dihydro-15-keto-16,16-difluoro-PGE$_1$ | 0.2 |
| nonion surfactant | 2 |
| distilled water | 98 |

The above ingredients were mixed and sterilized to give and injectable solution.

Formulation Example 3

(Enteric capsules)

13,14-dihydro-15-keto-16,16-difluoro-20-methyl-PGE$_2$ (50 mg) dissolved in methanol (10 ml) was mixed with mannitol (18.5 g). The mixture was screened (with a sieve, the pore size of which being 30 mm in diameter), dried at 30° C. for 90 minutes and screened again. The powders thus obtained were mixed with fine-grain silica gel (Aerosil*, 200 g) and filled in No.3 hard gelatin capsules (100) to give enteric capsules which contain 0.5 mg of 13,14-dihydro-15-keto-16,16-difluoro-20-methyl-PGE$_2$ per capsule.

*Trade Mark

Formulation Example 4

(Powders for oral administration)

|  | (Parts by weight) |
|---|---|
| 13,14-dihydro-6,15-diketo-16,16-difluoro-PGE$_1$ methyl ester | 5 |
| light anhydrous silicic acid | 5 |
| Abicel* | 20 |
| lactose | 70 |

*Trade Mark

The above ingredients were mixed to give powders for oral administration.

Formulation Example 5

(Soft gelatine capsules)

| | (Parts by weight) |
|---|---|
| 13,14-dihydro-6,15-diketo-19-methyl-PGE$_1$ methyl ester | 1 |
| light anhydrous silicic acid | 899 |
| Panasate* | 20 |

*Trade Mark

The above ingredients were mixed and filled in soft gelatine capsules.

Formulation Example 6

(Enteric capsules)

16-desbutyl-13,14-dihydro-15-keto-16-m-trifluoromethylphenoxy-PGF$_{2\alpha}$ methyl ester (50 mg) dissolved in methanol (10 ml) was mixed with mannitol (18.5 g). The mixture was screened (with a sieve, the pore size of which being 30 mm in diameter), dried at 30° C. for 90 minutes and screened again. The powders thus obtained were mixed with fine-grain silica gel (Aerosil*, 200 g) and filled in No.3 hard gelatin capsules (100) to give enteric capsules which contain 0.5 mg of 13,14-dihydro-15-keto-16-desbutyl-16-m-trifluoromethylphenoxy-PGF$_{2\alpha}$ methyl ester per capsule.

*Trade Mark

Formulation Example 7

(Powders for injection)

| | (Parts by weight) |
|---|---|
| 13,14-dihydro-15-keto-16,16-difluoro-PGE$_1$ | 1 |
| mannitol | 5 |
| distilled water | 0.4 |

The above ingredients were mixed, stirred, sterilized, filtered and lyophilized to give powders for injection.

Formulation Example 8

(Injectable solution)

| | (Parts by weight) |
|---|---|
| 13,14-dihydro-6,15-diketo-5R,S-difluoro-PGE$_1$ | 0.2 |
| nonion surfactant | 2 |
| distilled water | 98 |

The above ingredients were mixed and sterilized to give and injectable solution.

Formulation Example 9

(Powders for oral administration)

| | (Parts by weight) |
|---|---|
| 13,14-dihydro-15-keto-16,16-difluoro-19-desmethyl-PGE$_2$ methyl ester | 5 |
| light anhydrous silicic acid | 5 |
| Abicel* | 20 |
| lactose | 70 |

*Trade Mark

The above ingredients were mixed to give powders for oral administration.

Formulation Example 10

(Soft gelatine capsules)

| | (Parts by weight) |
|---|---|
| 13,14-dihydro-15-keto-16-desbutyl-16-m-trifluoromethylphenoxy-PGE$_2$ methyl ester | 1 |
| light anhydrous silicic acid | 899 |
| Panasate* | 20 |

*Trade Mark

The above ingredients were mixed and filled in soft gelatine capsules.

In the above formulation examples, the active ingredient can be replaced by any other compound within the compounds used in the invention.

Formulation Example 11

(Ophthalmic solution)

| | |
|---|---|
| 13,14-dihydro-15-keto-20-ethyl-PGF$_{2\alpha}$ | 10 mg |
| Physiological Saline | 10 ml |

The above components were placed in separate vials. The vials were combined for preparing a solution on actual use.

Test Example 1

Wistar rats (3 weeks old, weight: 40 to 50 g) were allotted into 3 group, each group consisting of 5 or 6 animals (i.e. 10 or 12 eyes). The group 1 was assigned to the normal control group and fed with normal diet. The groups 2 and 3 were fed with 50% galactose diet.

The group 2 subcutaneously received 2 times 5 ml/kg doses (morning and evening) of pure physiological saline, while the group 3 received similarly 2 times doses of 10 μg/kg test compound dissolved in 5 mg/kg physiological saline.

As the test compound, 13,14-dihydro-15-keto-16,16-difluoro-PGE$_2$ was used.

The eyes of the rats were observed every day and the day on which the nucleus of crystalline lens was distinctly opaque as compared with nuclei of the group 1 animals (control) was taken as the day of onset of cataract. The results are shown in Table 1, in which the numerical values indicate cataract/total eyes.

TABLE 1

| Group (n) | Day | | | | | | |
|---|---|---|---|---|---|---|---|
| | 1 | — | 6 | 7 | 8 | 9 | 10 |
| 1 (6) | 0/12 | — | 0/12 | 0/12 | 0/12 | 0/12 | 0/12 |
| 2 (5) | 0/10 | — | 0/10 | 1/10 | 2/10 | 5/10 | 7/10 |
| 3 (6) | 0/12 | — | 0/12 | 0/12 | 0/12 | 1/12 | 1/12 |

It can be seen from the above results that the test compound has an activity inhibiting experimental cataract.

Test Example 2

Wistar rats (3 weeks old, weight: 40 to 50 g) were allotted into 5 groups, each group consisting of 6 animals (i.e. 12 eyes). Each group was fed with 30% galactose diet.

The eyes of the rats were observed every day and the day on which the nucleus of crystalline lens was distinctly opaque. Test design was as follows:

| Group | Substance | Dose/Administration | Mode |
|---|---|---|---|
| 1 | Physiological Saline | 5 tl/eye | opthalmic |
| 2 | Test Compound 1 | 0.1 tg/eye | opthalmic |
| 3 | Test Compound 1 | 10 tg/kg | subcutaneous |
| 4 | Test Compound 2 | 6 tg/eye | opthalmic |
| 5 | Test Compound 3 | 100 tg/kg | subcutaneous |

Test Compounds:
1: 13,14-dihydro-15-keto-16,16-difluoro-$PGE_2$ methyl ester
2: 13,14-dihydro-15-keto-20-ethyl-$PGF_{2\alpha}$ isopropyl ester
3: 13,14-dihydro-15-keto-20-ethyl-$PGF_{2\alpha}$ The ophthalmic administration was effected with a solution of the test compound dissolved in a physiological saline (5 tl/eye), administered 3 times a day. The subcutaneous administration was effected with a solution of the test compound in a physiological saline (5 ml/kg), administered twice a day.

The results are shown in Table 2, in which the numerical values indicate cataract/total eyes.

TABLE 2

| Group | Day |  |  |  |  |  |
|---|---|---|---|---|---|---|
|  | 1 | — | 11 | 12 | 13 | 14 |
| 1 | 0/12 | — | 2/12 | 5/12 | 8/12 | 9/12 |
| 2 | 0/12 | — | 0/12 | 3/12 | 4/12 | 5/12 |
| 3 | 0/12 | — | 0/12 | 0/12 | 1/12 | 1/12 |
| 4 | 0/12 | — | 1/12 | 2/12 | 5/12 | 5/12 |
| 5 | 0/12 | — | 1/12 | 3/12 | 5/12 | 6/12 |

It can be seen from the above results that the test compounds have an activity inhibiting experimental cataract.

Test Example 3

Wistar rats (3 weeks old, weight: 40 to 50 g) were allotted into 3 groups, each group consisting of 6 animals (i.e. 12 eyes). Each group was fed with 30% galactose diet.

The eyes of the rats were observed every day and the day on which the nucleus of crystalline lens was distinctly opaque.

Test design was as follows:

| Group | Substance | Dose/Administration | Mode |
|---|---|---|---|
| 1 | Physiological Saline | 5 tl/eye | ophthalmic |
| 2 | Test Compound 4 | 0.1 tg/eye | ophthalmic |
| 3 | Test Compound 4 | 10 tg/kg | subcutaneous |

Test Compound:
4: 13,14-dihydro-15-keto-16,16-difluoro-$PGE_2$ isopropyl ester

The ophthalmic administration was effected with a solution of the test compound dissolved in a physiological saline (5 tl/eye), administered 3 times a day. The subcutaneous administration was effected with a solution of the test compound in a physiological saline (5 ml/kg), administered twice a day.

The results are shown in Table 3, in which the numerical values indicate rate (in %) of onset of cataract (cataract× 100/total eyes).

TABLE 3

| Group | Day |  |  |  |  |  |
|---|---|---|---|---|---|---|
|  | 1 | — | 13 | 14 | 15 | 16 | 17 |
| 1 | 0 | — | 8 | 33 | 75 | 75 | 92 |
| 2 | 0 | — | 0 | 0 | 17 | 25 | 33 |
| 3 | 0 | — | 0 | 8 | 8 | 17 | 17 |

It can be seen from the above results that the test compounds have an activity inhibiting experimental cataract.

Test Example 4

Wistar rats (3 weeks old, weight: 40 to 50 g) were allotted into 3 groups, each group consisting of 6 animals (i.e. 12 eyes). Each group was fed with 30% galactose diet.

The eyes of the rats were observed every day and the day on which the nucleus of crystalline lens was distinctly opaque.

Test design was as follows:

| Group | Substance | Dose/Administration | Mode |
|---|---|---|---|
| 1 | Physiological Saline | 5 ml/kg | subcutaneous |
| 2 | Test Compound 5 | 0.1 tg/eye | ophthalmic |
| 3 | Test Compound 5 | 10 tg/kg | subcutaneous |

Test Compounds:
5: 13,14-dihydro-15-keto-16,16-difluoro-$PGE_1$ methyl ester

The ophthalmic administration was effected with a solution of the test compound dissolved in a physiological saline (5 tl/eye), administered 3 times a day. The subcutaneous administration was effected with a solution of the test compound in a physiological saline (5 ml/kg), administered 4 times a day.

The results are shown in Table 4, in which the numerical values indicate rate (in %) of onset of cataract (cataract× 100/total eyes).

TABLE 4

| Group | Day |  |  |  |  |  |
|---|---|---|---|---|---|---|
|  | 1 | — | 14 | 15 | 16 | 17 | 18 |
| 1 | 0 | — | 8 | 8 | 33 | 50 | 67 |
| 2 | 0 | — | 0 | 0 | 8 | 17 | 25 |
| 3 | 0 | — | 0 | 0 | 17 | 25 | 33 |

It can be seen from the above results that the test compounds have an activity inhibiting experimental cataract.

Test Example 5 (Comparative)

Wistar rats (3 weeks old, weight: 40 to 50 g) were allotted into 7 groups. Each group was fed with 40% galactose diet.

The eyes of the rats were observed every day and the day on which the nucleus of crystalline lens was distinctly opaque.

Test design was as follows:

| Group | Substance | Animal (eye) | Dose/Administration |
|---|---|---|---|
| 1 | Physiological Saline | 10(20) | 5 ml/kg |
| 2 | Test Compound 6 | 5(10) | 100 tg/kg |
| 3 | Test Compound 7 | 5(10) | 100 tg/kg |

-continued

| Group | Substance | Animal (eye) | Dose/Administration |
|---|---|---|---|
| 4 | Test Compound 8 | 5(10) | 100 tg/kg |
| 5 | Test Compound 9 | 5(10) | 100 tg/kg |
| 6 | Test Compound 10 | 5(10) | 10 tg/kg |
| 7 | Test Compound 11 | 5(10) | 1 tg/kg |

Test Compounds:
6: $PGE_1$
7: $PGD_2$
8: $PGF_{2\alpha}$
9 $PGA_2$
10: 16,16-dimethyl-$PGE_2$
11: 6-oxo-17S,20-dimethyl-$PGE_1$ The administration was effected with a solution of the test compound in a physiological saline (5 ml/kg), substaneously administered twice a day.

The results are shown in Table 5, in which the numerical values indicate rate (in %) of onset of cataract (cataract× 100/total eyes).

TABLE 5

| Group | Day | | | | | | |
|---|---|---|---|---|---|---|---|
| | 1 | — | 9 | 10 | 11 | 12 | 13 |
| 1 | 0 | — | 5 | 25 | 45 | 50 | 75 |
| 2 | 0 | — | 10 | 20 | 70 | 100 | 100 |
| 3 | 0 | — | 10 | 10 | 40 | 60 | 80 |
| 4 | 0 | — | 10 | 30 | 50 | 60 | 60 |
| 5 | 0 | — | 10 | 10 | 50 | 70 | 90 |
| 6 | 0 | — | 50 | 70 | 70 | 80 | 90 |
| 7 | 0 | — | 0 | 30 | 60 | 70 | 70 |

It can be seen from the above results that the primary type PGs having a hydroxy group at position 15 have no distinct inhibition and in some cases have rather promotion to cataract.

Test Example 6

Wistar rats (3 weeks old, weight: 40 to 50 g) were allotted into 4 groups, each group consisting of 9 animals (i.e. 18 eyes). Each group was fed with 30% galactose diet.

The eyes of the rats were observed every day and the day on which the nucleus of crystalline lens was distinctly opaque.

Test design was as follows:

| Group | Substance | Dose/Administration |
|---|---|---|
| 1 | Physiological Saline | 5 tl/eye |
| 2 | Test Compound 12 | 0.1 tl/eye |
| 3 | Test Compound 13 | 0.1 tg/eye |
| 4 | Test Compound 14 | 1.0 tg/eye |

Test Compounds:
12: 13,14-dihydro-15-keto-16,16-difluoro-19-desmethyl-$PGE_2$ methyl ester
13: 13,14-dihydro-15-keto-16,16-difluoro-20-methyl-$PGE_2$ methyl ester
14: 13,14-dihydro-15-keto-16,16-difluoro-20-ethyl-$PGE_2$ methyl ester The administration was effected with a solution of the test compound in a physiological saline (5 tl/eye), administered 3 times a day. The control group received a physiological saline (5 tl/eye).

The results are shown in Table 6, in which the numerical values indicate rate (in %) of onset of cataract (cataract× 100/total eyes).

TABLE 6

| Group | Day | | | | |
|---|---|---|---|---|---|
| | 1 | — | 14 | 15 | 16 |
| 1 | 0 | — | 44 | 61 | 67 |
| 2 | 0 | — | 11 | 17 | 17 |
| 3 | 0 | — | 28 | 33 | 33 |
| 4 | 0 | — | 6 | 22 | 28 |

It can be seen from the above results that the test compounds have an activity inhibiting experimental cataract.

Test Example 7

Wistar rats (3 weeks old, weight: 50 to 60 g) were allotted into 6 groups, each group consisting of 9 animals (i.e. 8 eyes). Each group was fed with 30% galactose diet.

The eyes of the rats were observed every day and the day on which the nucleus of crystalline lens was distinctly opaque.

Test design was as follows:

| Group | Substance | Dose/Administration |
|---|---|---|
| 1 | Physiological Saline | 5 ml/kg |
| 2 | Test Compound 15 | 10 tg/kg |
| 3 | Test Compound 16 | 10 tg/kg |
| 4 | Test Compound 17 | 10 tg/kg |
| 5 | Test Compound 18 | 10 tg/kg |
| 6 | Test Compound 19 | 10 tg/kg |

Test Compounds:
15: 13,14-dihydro-15-keto-16,16-difluoro-$PGE_1$ isopropyl ester
16: 13,14-dihydro-15-keto-16,16-difluoro-20-ethyl-$PGE_1$ isopropyl ester
17: 2-decarboxy-2-(2-carboxyethyl)-13,14-dihydro-15-keto-16,16-difluoro-$PGE_1$ isopropyl ester
18: 2-decarboxy-2-(2-carboxyethyl)-13,14-dihydro-15-keto-16,16-difluoro-20-ethyl-$PGE_1$ isopropyl ester
19: 13,14-dihydro-15-keto-16,16-dimethyl-$PGE_2$ ethyl ester The administration was effected with a solution of the test compound in a physiological saline (5 ml/kg), administered twice a day. The control group received a physiological saline (5 ml/kg).

The results are shown in Table 7, in which the numerical values indicate rate (in %) of onset of cataract (cataract× 100/total eyes).

TABLE 7

| Group | Day | | | | |
|---|---|---|---|---|---|
| | 1 | — | 12 | 13 | 14 |
| 1 | 0 | — | 22 | 39 | 50 |
| 2 | 0 | — | 6 | 6 | 28 |
| 3 | 0 | — | 6 | 11 | 28 |
| 4 | 0 | — | 11 | 22 | 28 |
| 5 | 0 | — | 6 | 11 | 22 |
| 6 | 0 | — | 17 | 17 | 39 |

It can be seen from the above results that the test compounds have an activity inhibiting experimental cataract.

What we claim is:

1. A method for treatment of cataract which comprises administering to a subject in need of such treatment, a 15-ketoprostaglandin compound in an amount effective in treatment of cataract, wherein said compound is of formula (I):

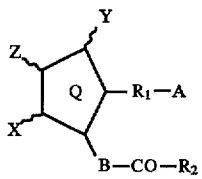

wherein X and Y are hydrogen, hydroxy, halo, lower alkyl, hydroxy(lower)alkyl or oxo, with the proviso that at least one of X and Y is a group other than hydrogen, the 5-membered ring Q may have at least one double bond, Z is hydrogen or halo, A is —CH$_2$—OH, —COCH$_2$OH, —COOH, salt thereof, ester thereof or amide thereof, B is —CH$_2$—CH$_2$—, R$_1$ is a bivalent saturated or unsaturated, lower or medium aliphatic hydrocarbon residue which is unsubstituted or substituted with halo, oxo or aryl and R$_2$ is a saturated or unsaturated, lower or medium aliphatic hydrocarbon residue which is unsubstituted or substituted with halo, hydroxy, oxo, lower alkoxy, lower alkanoyloxy, cyclo(lower)alkyl, aryl or aryloxy.

2. The method of claim 1, wherein said 15-ketoprostaglandin compound is a 16-monohalo-15-ketoprostaglandin compound or a 16-dihalo-15-ketoprostaglandin compound.

3. The method of claim 1, wherein said 15-ketoprostaglandin compound is a 13,14-dihydro-16-monofluoro-15-ketoprostaglandin compound or a 13,14-dihydro-16-difluoro-15-ketoprostaglandin compound.

4. The method of claim 1, wherein said 15-ketoprostaglandin compound is a 15-keto-20-lower alkyl-prostaglandin compound.

5. The method of claim 1, wherein said 15-ketoprostaglandin compound is a 16-di-lower alkyl-prostaglandin compound.

* * * * *